(12) United States Patent
Paperno et al.

(10) Patent No.: US 10,702,073 B2
(45) Date of Patent: Jul. 7, 2020

(54) PORTABLE ROCKER FOR NEWBORN BABY OR INFANT

(71) Applicant: Steven Paperno, Westlake Village, CA (US)

(72) Inventors: Steven Paperno, Westlake Village, CA (US); Joseph R. Adamski, Burbank, CA (US)

(73) Assignee: Steven Paperno, Westlake Village, CA (US)

( * ) Notice: Subject to any disclaimer, the term of this patent is extended or adjusted under 35 U.S.C. 154(b) by 318 days.

(21) Appl. No.: 15/901,495

(22) Filed: Feb. 21, 2018

(65) Prior Publication Data

US 2018/0325280 A1 Nov. 15, 2018

Related U.S. Application Data

(60) Provisional application No. 62/505,505, filed on May 12, 2017.

(51) Int. Cl.

| A47D 9/02 | (2006.01) |
| G08B 7/06 | (2006.01) |
| G05D 3/10 | (2006.01) |
| G05D 3/12 | (2006.01) |
| A61B 5/11 | (2006.01) |
| A61B 5/0205 | (2006.01) |
| A61B 5/024 | (2006.01) |
| A61B 5/08 | (2006.01) |
| A61B 5/00 | (2006.01) |

(52) U.S. Cl.
CPC .................. *A47D 9/02* (2013.01); *A61B 5/11* (2013.01); *G05D 3/10* (2013.01); *G05D 3/12* (2013.01); *G08B 7/06* (2013.01); *A61B 5/0002* (2013.01); *A61B 5/024* (2013.01); *A61B 5/0205* (2013.01); *A61B 5/0816* (2013.01); *A61B 5/4809* (2013.01); *A61B 5/6891* (2013.01); *A61B 5/746* (2013.01); *A61B 2503/04* (2013.01); *A61B 2503/045* (2013.01); *A61B 2562/0219* (2013.01)

(58) Field of Classification Search
CPC ........................................................ A47D 9/02
USPC .............................................. 5/105–109, 655
See application file for complete search history.

(56) References Cited

U.S. PATENT DOCUMENTS

| 5,845,350 A * | 12/1998 | Beemiller ................ A47D 9/02 5/109 |
| 6,155,976 A | 12/2000 | Sackner et al. |
| 7,958,579 B2 * | 6/2011 | Westerkamp ............ A47D 9/02 5/105 |

(Continued)

*Primary Examiner* — Fredrick C Conley
(74) *Attorney, Agent, or Firm* — Knobbe, Martens, Olson & Bear LLP

(57) ABSTRACT

A rocker for supporting an infant or other item includes a carrier assembly and a support assembly. The carrier assembly has a support platform. The support assembly is disposed below the carrier assembly is operable to selectively impart motion to the carrier assembly in a plurality of different motion patterns. The motion patterns can include one or more of translation along a first linear direction, translation along a second linear direction perpendicular to the first linear direction, yaw relative to a first axis, pitch relative to a second axis that is perpendicular to the first axis, roll about a third axis that is perpendicular to the first and second axes, and elevation changes relative to the support assembly.

20 Claims, 15 Drawing Sheets

(56) References Cited

U.S. PATENT DOCUMENTS

| | | | |
|---|---|---|---|
| 2013/0229040 A1* | 9/2013 | Mountz | A47C 9/02 297/260.2 |
| 2015/0045608 A1 | 2/2015 | Karp et al. | |
| 2016/0165961 A1 | 6/2016 | Karp | |
| 2016/0166081 A1 | 6/2016 | Karp et al. | |
| 2016/0174728 A1 | 6/2016 | Karp et al. | |
| 2017/0043117 A1 | 2/2017 | Karp et al. | |
| 2017/0043118 A1 | 2/2017 | Karp et al. | |

\* cited by examiner

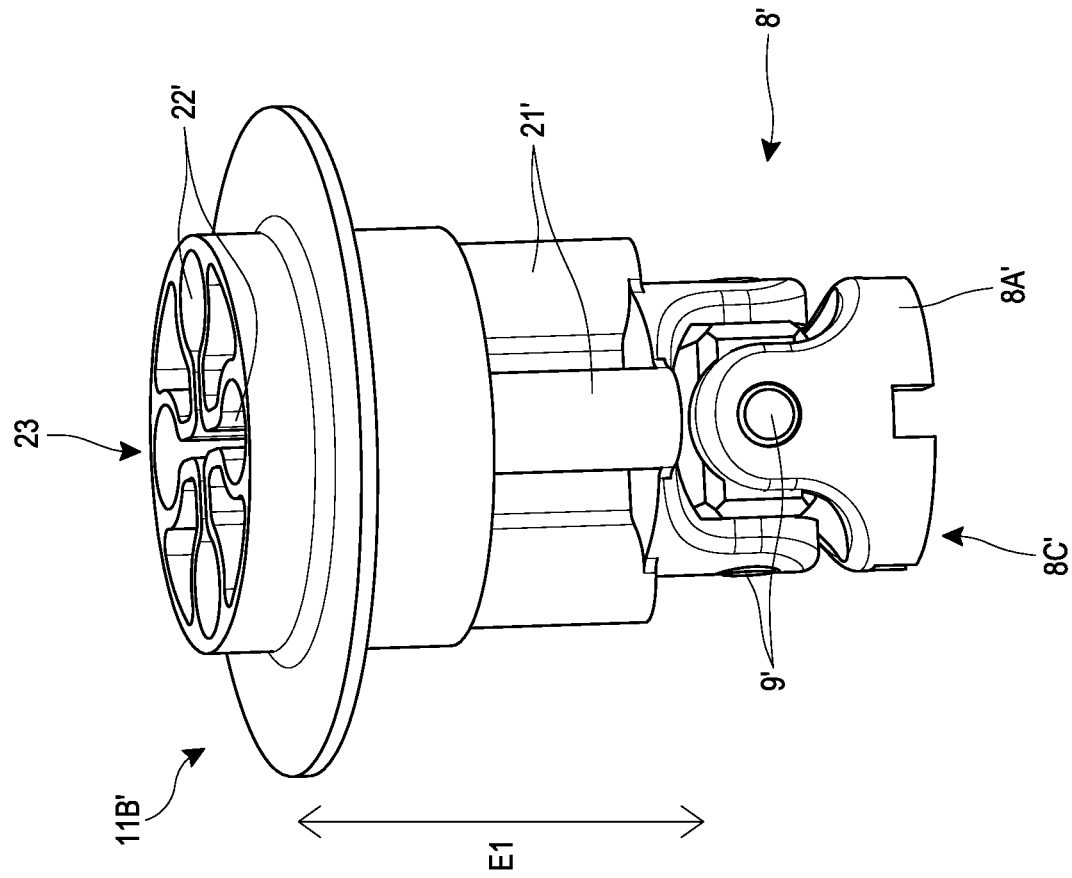
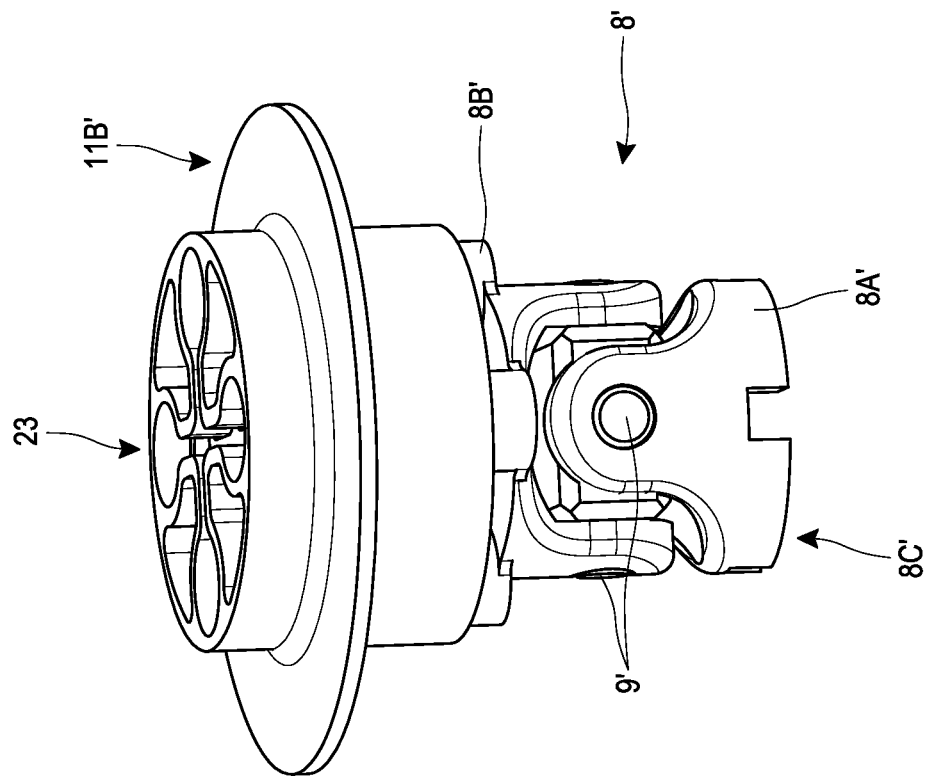
FIG. 12B
FIG. 12A

PORTABLE ROCKER FOR NEWBORN BABY OR INFANT

CROSS-REFERENCE TO RELATED APPLICATIONS

Any and all applications for which a foreign or domestic priority claim is identified in the Application Data Sheet as filed with the present application are hereby incorporated by reference under 37 CFR 1.57, and should be considered a part of this specification.

BACKGROUND

Field

The present invention is directed to a portable rocker, and more particularly to a portable rocker for use with newborn babies (e.g., with premature newborn babies in a hospital incubator) or infants (e.g., at home, while traveling, in a hospital, in a day care facility).

Description of the Related Art

Movement of newborn babies is important, which is why newborns are regularly picked up and held by nurses in a hospital nursery. Movement can also soothe newborns, who are accustomed to being in motion while in the womb. Additionally, movement can help calm newborn babies and infants and help them to sleep, which is why rocking of babies or driving them in a car can help them to fall asleep. However, it may not be possible to give newborn babies and infants individual and constant attention (e.g., due to staffing levels in a hospital). Also, with premature newborn babies, who are placed in hospital incubators, it may not be possible to regularly pick them up due to their delicate state.

SUMMARY

There is a need for an improved mechanism that can impart motion to newborn babies and infants, such as in a hospital setting (e.g., in an incubator, nursery, pediatric intensive care unit), at home (e.g., in a crib, bassinet) or in a day care (e.g., in a crib, bassinet).

In accordance with one aspect, a portable rocker assembly is provided that can impart motion in various degrees of freedom onto a newborn baby or infant supported on the rocker assembly. Such motion can soothe the newborn baby or infant and allow them to more quickly fall asleep and/or to sleep more soundly. In one aspect, the portable rocker can impart one or more of lateral translation, vertical translation, pivoting about a roll axis, pivoting about a pitch axis, pivoting about a yaw axis, or a combination of these.

In accordance with another aspect, a rocker for supporting an infant or includes a carrier assembly and a support assembly. The carrier assembly has a support platform with a generally planar top surface. The support assembly is disposed below the carrier assembly and configured for placement on a planar surface. The support assembly is configured to impart motion to the carrier assembly in a motion pattern. The motion pattern includes one or more of translation along a first linear direction, translation along a second linear direction perpendicular to the first linear direction, yaw relative to the axis, pitch relative to a second axis that is perpendicular to the first axis, roll about a third axis that is perpendicular to the first and second axes, and elevation changes relative to the support assembly.

In accordance with another aspect, a rocker with a carrier assembly includes a support platform and an opening on a bottom surface of the support platform. A support assembly is disposed below the carrier assembly and can be placed on a planar surface. The support assembly can impart motion to the carrier assembly in one or more of 1) yaw about a first axis that extends through the opening, 2) pitch about a second axis that is perpendicular to the first axis, 3) roll about a third axis that is perpendicular to the first and second axes, and 4) elevation changes above the support assembly. The support assembly can include a base platform and a frame that moves on the base platform and operates to provide yaw about the first axis. A joint with a lower yoke is mounted on the frame and an upper yoke is slideably coupled within the opening of the support platform. The upper yoke engages the opening to impart said rotation about the first axis to the carrier assembly based on rotation of the frame. A plurality of motor assemblies is mounted on the frame. Each of the motor assemblies engages the bottom surface of the support platform. Optionally, each of the motor assemblies actuates independently of the other motor assemblies. An electronic controller unit controls an operation of the plurality of motor assemblies to impart one or more of 1) pitch, 2) roll, and 3) elevation changes on the carrier assembly.

BRIEF DESCRIPTION OF THE DRAWINGS

FIG. 5 is a right side view of the rocker assembly of FIG. 1, the left side view being similar.

FIGS. 12A and 12B are perspective view of a universal joint and coupling in first and second configurations, respectively.

DETAILED DESCRIPTION

Figure 1:
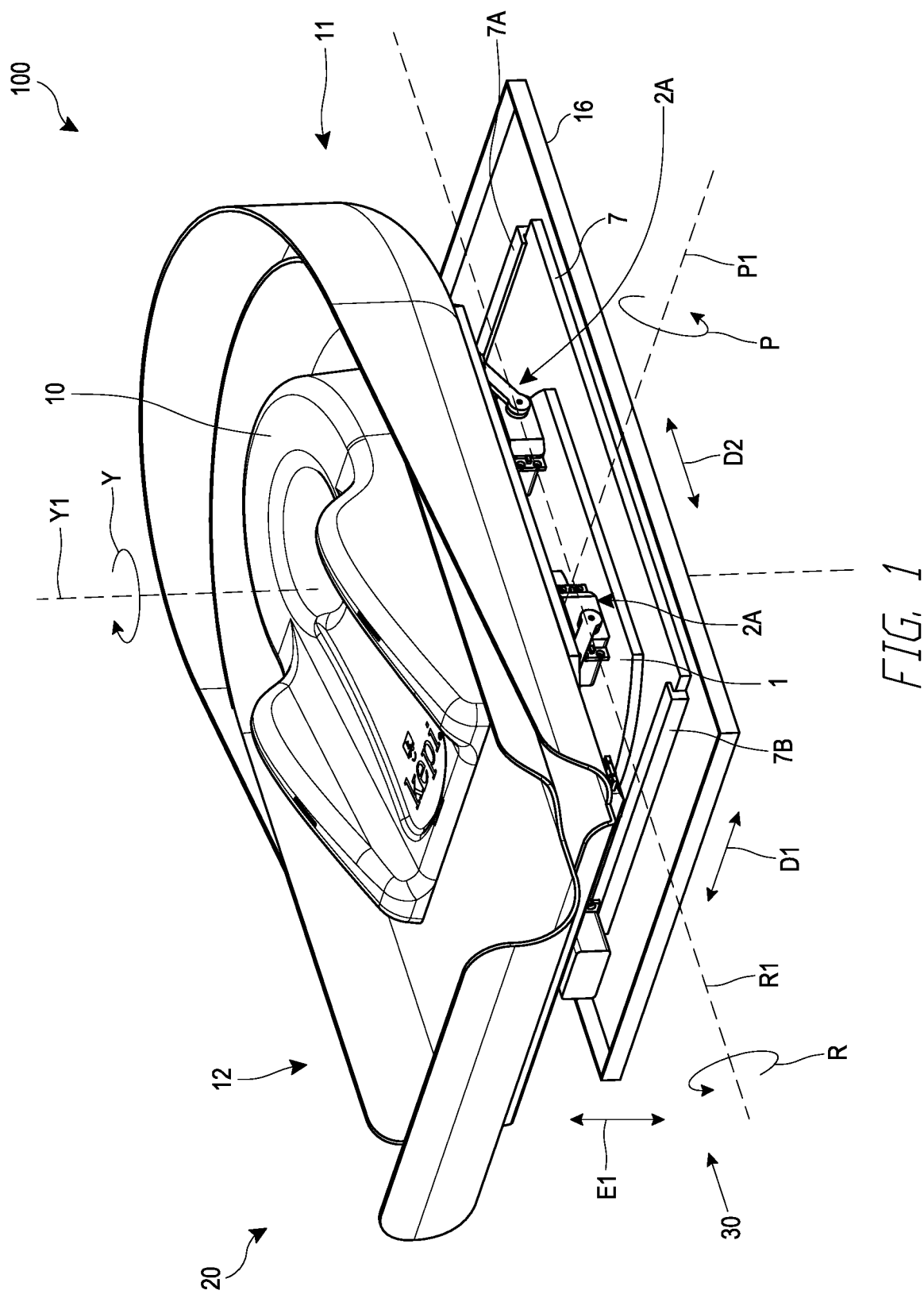
FIG. 1 is a perspective assembled view of a rocker assembly.
Figure 2:
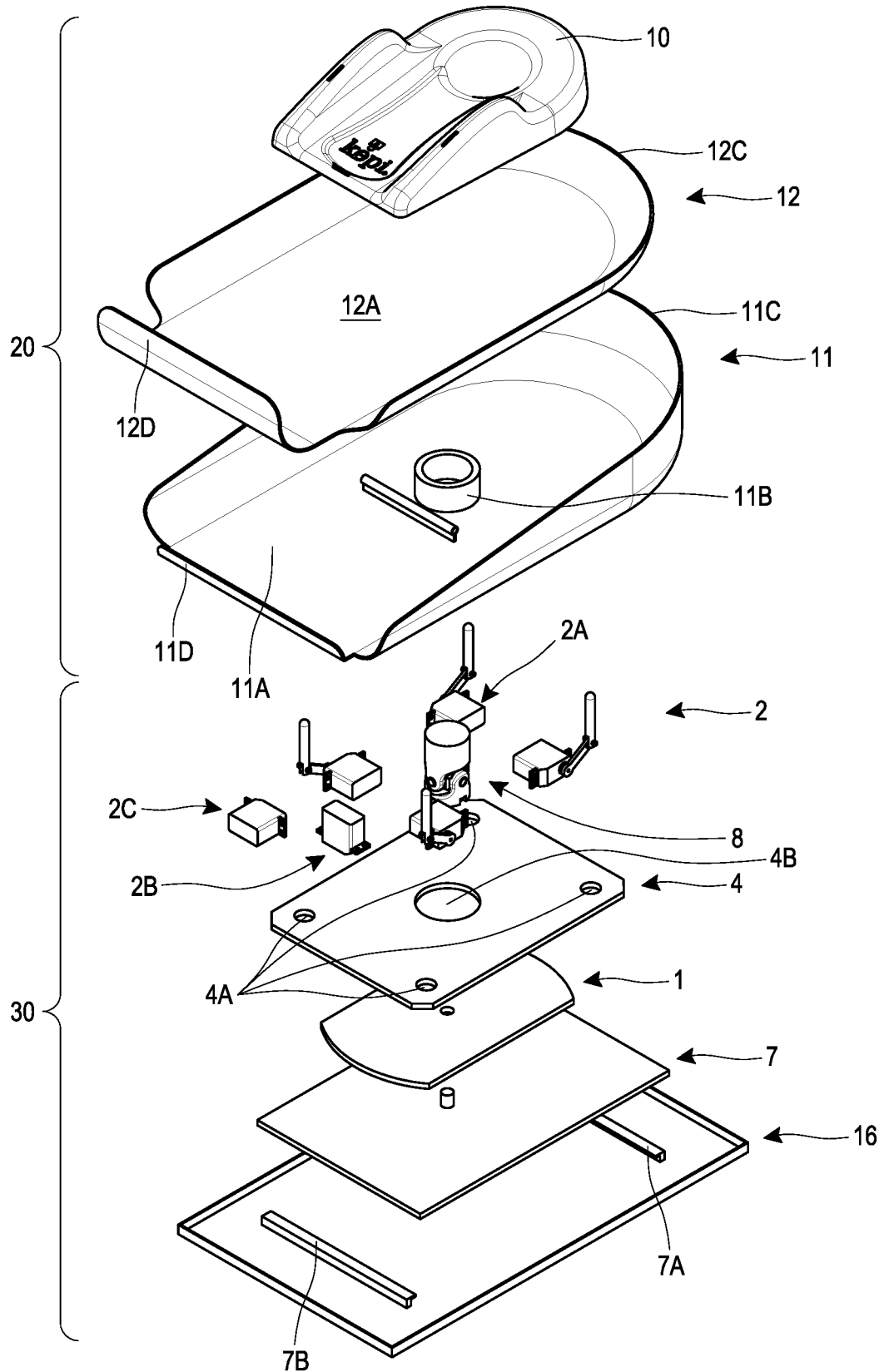
FIG. 2 is a perspective exploded view of the rocker assembly of FIG. 1.

FIGS. 1-6 show a rocker assembly 100. The rocker assembly 100 can have carrier assembly 20 and a support assembly 30. The carrier assembly 20 can provide support to an infant or other object. The carrier assembly 20 can optionally be coupled with the support assembly 30 at least in part by a joint 8 (e.g., a universal joint). The support assembly 30 can optionally include the joint 8 and provide support and movement to the carrier assembly 20, as described below.

The support assembly 30 can include a base 16 (e.g., a base platform). The base 16 can be placed on a surface (e.g., flat surface) and provide stability to the rocker 100. A first translation platform 7 can be disposed above the base 16 and can move relative to the base 16. The first translation platform 7 can translate relative to a base platform 16 in a first direction D1 (e.g., a direction D1 generally transverse to a longitudinal axis of the carrier assembly 20). One or more sleeves 7A, 7B (or tracks) can provide stability and/or guidance to the sliding motion of the first translation platform 7 and can couple the first translation platform 7 with the base 16.

Figure 4:
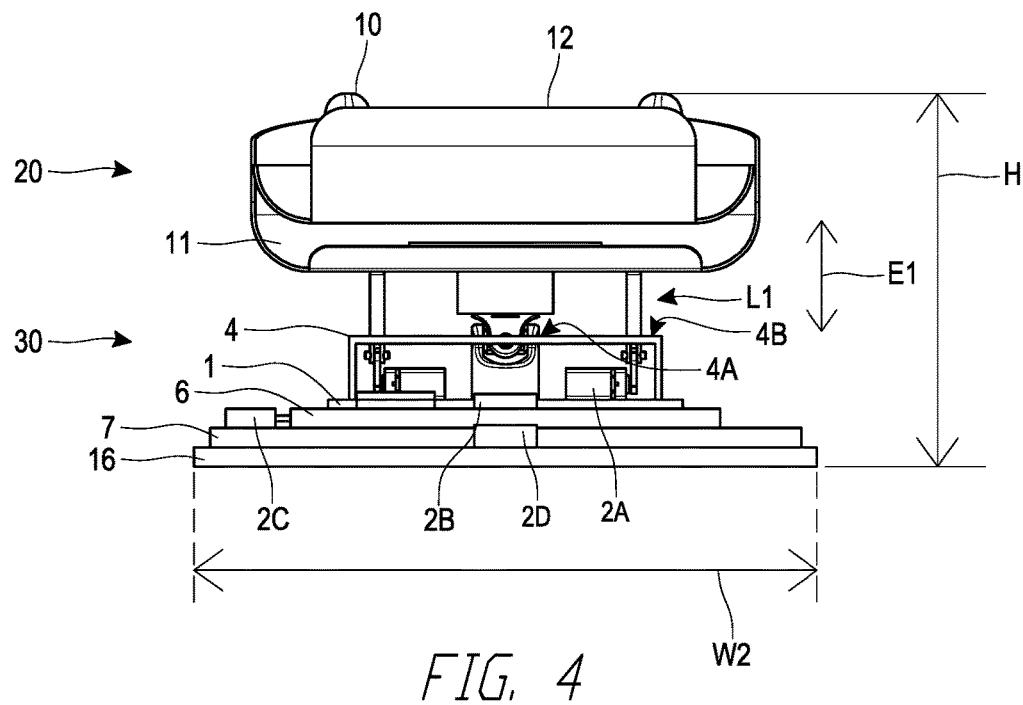
FIG. 4 is a front view of the rocker assembly of FIG. 1.
Figure 5:
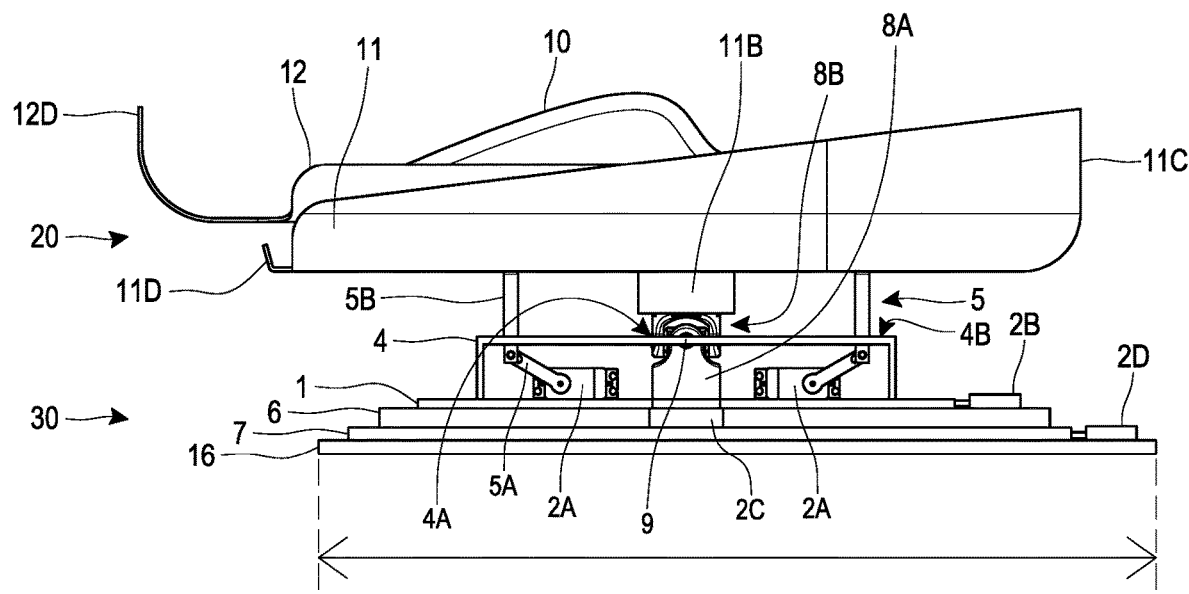

In some embodiments, as shown in FIGS. 4-5, a second translation platform 6 can be disposed on the first translation platform 7. The second translation platform 6 can translate relative to the first translation platform 7 in a second direction D2 (e.g., a direction D1 generally transverse to the first direction D1). Similar to the sleeves 7A, 7B, one or more sleeves (or tracks) can provide stability and/or guidance to the sliding motion of the second translation platform 6 and couple the second translation platform 6 with the first translation platform 7. In some implementations, the first and second directions D1, D2 can be perpendicular. In some implementations, the rocker assembly 100 includes only one (or no) translation platforms 6, 7.

With continued reference to FIGS. 1-6, a motor platform 1 can be disposed over (e.g., on top of) the second translation platform 6 (where included). Where the second translation platform 6 is excluded, the motor platform 1 can be disposed over (e.g., on top of) the first translation platform 7. Where the first and second translation platforms 7, 6 are excluded, the motor platform 1 can be disposed over (e.g., on top of) the base 16. The motor platform 1 optionally extends along a parallel plane to one or more of the first translation platform 7, second translation platform 6 and base 16. Optionally, the motor platform 1 can rotate with respect to its support in direction Y1 along a plane substantially parallel to the base 16 and/or parallel to an upper surface of the second translation platform 6. The rotation of the motor platform 1 can optionally be transferred to the carrier assembly 20 by the joint 8 so that rotation of the motor platform 1 effects rotation of the carrier assembly 20 (e.g., about a yaw axis Y). In some implementations, the joint 8 is optionally coupled to the motor platform 1 substantially at the center of rotation of the motor platform 1.

A plurality of motor assemblies 2 (e.g., electric motor assemblies) can provide motion (e.g., a roll motion R about a roll axis R1, a pitch motion P about a pitch axis P1) to the carrier assembly 20. Motor assemblies 2A can be mounted on the motor platform 1 and provide support and/or movement to the carrier assembly 20. Each motor assembly 2A can include a driver assembly 5. In one implementation, the driver assembly 5 can include a drive arm 5A and a drive rod 5B. The drive arm 5A can be coupled with a motor (e.g., servo motor) of the motor assembly 2A (e.g., with an output shaft of the motor assembly 2A) on one end. On another end, the drive arm 5A can be coupled (e.g., pivotally coupled) with the drive rod 5B. The drive rod 5B can engage (e.g., operatively contact, directly contact) the carrier assembly 20 (e.g., a lower surface of a carrier support 11). Optionally, the drive rod 5B engages a cupped portion (e.g., a recessed portion) on a bottom surface of the carrier support 11.

The motor assemblies 2A of the support assembly 30 can effect movement in a roll R direction and a pitch P direction (e.g., via a plurality of servo motors) by movement of the drive rods 5B up and down via the drive arms 5A. In the illustrated embodiment, four servo motors are mounted on the motor platform 1. However, in other implementations more or fewer servo motors, or other type of motors, can be used to effect movement in the roll R direction and/or pitch P direction.

The joint 8 (e.g., universal joint) can optionally mount to the motor platform 1. A lower yoke 8A of the joint 8 (e.g., universal joint yoke) can optionally be fixedly coupled in a center of the motor platform 1. Optionally, an upper yoke 8B can movably couple with the carrier assembly 20. The upper yoke 8B can extend at least partially through a central opening 11B in the carrier assembly 20 and be slideably engaged therewith. In this manner, the carrier assembly 20 can be raised and lowered (e.g., in elevation) by the motors assemblies 2A relative to the motor platform 1 without disengaging the upper yoke 8B from the carrier assembly 20.

A drive rod bearing platform 4 can optionally be disposed above the motor platform 1. The bearing platform 4 can provide stability to the driver assemblies 5 (e.g., drive rods 5B). The bearing platform 4 can have a plurality of openings 4A for slideably receiving the drive rods 5B. In some implementations, the openings 4A can be generally at the corners of the bearing platform 4. The bearing platform 4 can include a central opening 4B generally at a center of the bearing platform 4. The joint 8 can at least partially extend through the central opening 4B. In some implementations, the bearing platform 4 can include multiple layers (e.g., each with openings 4A) or shaft-like structures that provide support to the drive rods 5B and ensure that they translate without binding.

The arrangement of the first translation platform 7, the second translation platform 6, and the motor platform 1 is optional. In other implementations, the rotating platform can be on the bottom and the translation platforms can be located on top of the lowest platform, with the motor assemblies 2A coupled with the uppermost platform. In another implementation, the rotation platform can be sandwiched between the translation platforms. In other embodiments, one or more of the platforms is omitted.

The carrier assembly 20 of the rocker assembly 100 can include the carrier support 11. The carrier support 11 can optionally have a generally planar surface 11A, a central opening 11B, a circumferential wall 11C (e.g., that extends along a left side, a right side and a distal end of the carrier support 11) and/or a proximal curved wall 11D. The circumferential wall 11C can optionally taper from the distal end toward the proximal curved wall 11D, as best shown in FIG. 5. The central opening 11B can movably engage (e.g., slideably engage) at least a portion of the universal joint 8 (e.g., at least a portion of the upper yoke 8B can extend into the opening 11B on an underside of the carrier support 11).

Figure 3:
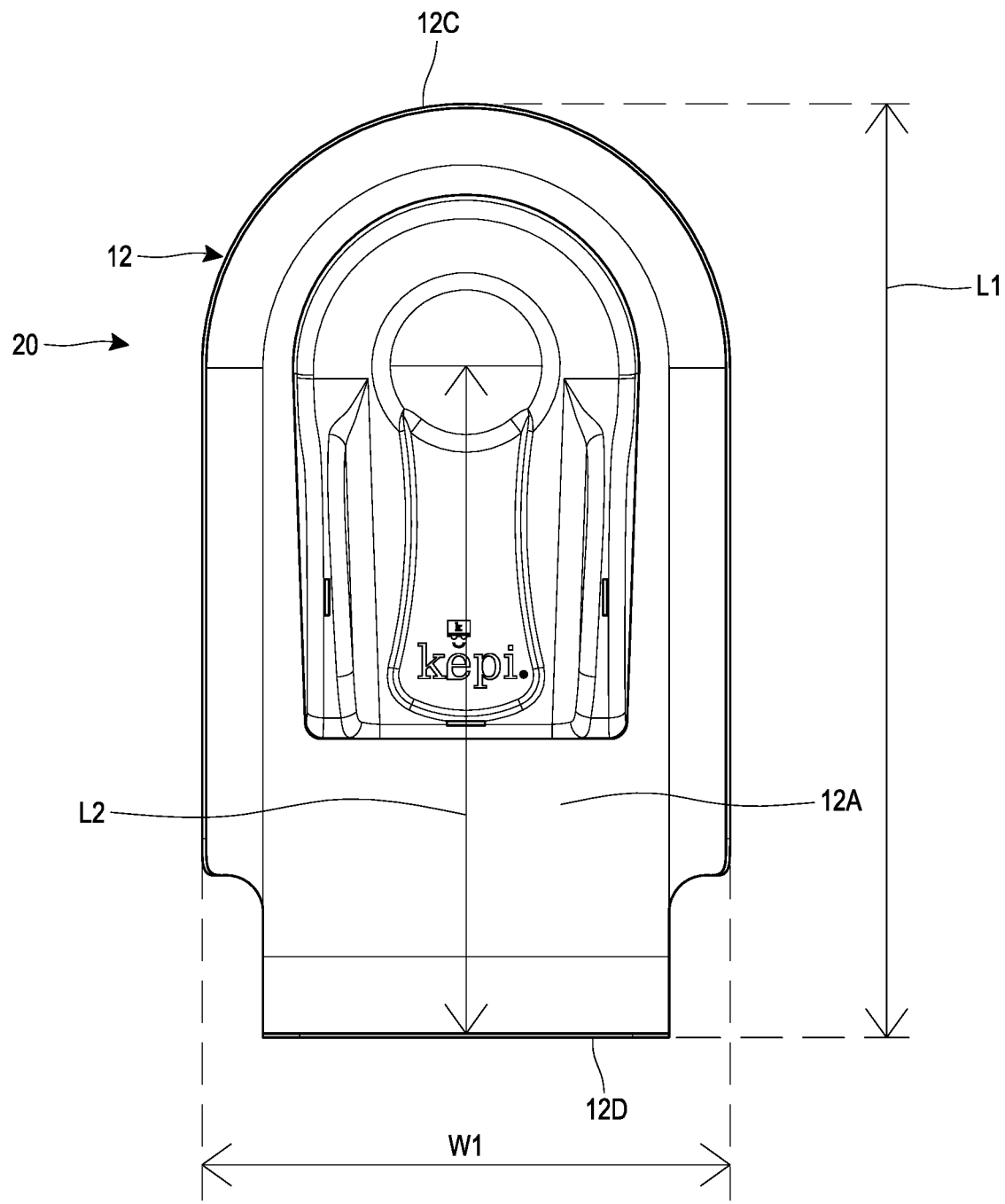
FIG. 3 is a top planar view of the rocker assembly of FIG. 1.

The carrier assembly 20 can optionally also include a carrier tray 12. The carrier tray 12 can at least partially fit in the carrier support 11 within the space defined by the circumferential wall 11C. The carrier tray 12 can be removably disposed in the carrier support 11 and can have a generally planar surface 12A, a circumferential wall 12C and a proximal curved wall 12D. In one implementation, the carrier tray 12 can be coupled to the carrier support 11 such that the planar surface 12A of the carrier tray 12 is inclined relative to the planar surface 11A of the carrier support 11. As best shown in FIG. 3, the upper edge of the circumferential wall 12C of the carrier tray 12 can be aligned with the upper edge of the circumferential wall 11C of the carrier support 11. In another implementation, shown in FIG. 2, the carrier tray 12 can be coupled to the carrier support 11 such that the planar surface 12A of the carrier tray 12 is relatively less inclined relative to the planar surface 11A of the carrier support 11. In another implementation, the carrier tray 12 is excluded.

Optionally, a dock member 10 can be removably coupled to the carrier tray 12, where the dock member 10 is disposed on the generally planar surface 12A. The dock member 10 can be removably coupled to the carrier tray 12 so that it does not move or shift on the planar surface 12A during motion of the rocker assembly 100 (e.g., the dock member 10 remains in a substantially fixed position on the carrier tray 12 when coupled thereto). Optionally, the underside of the dock member 10 can have one or more recesses that receive corresponding one or more protrusions on the generally planar surface 12A of the carrier tray 12 to substantially fix the position of the dock member 10 on the carrier tray 12 when coupled thereto. In another embodiment, the underside of the dock member 10 can have one or more protrusions that can extend through corresponding one or more openings or slots on the generally planar surface 12A of the carrier tray 12 to substantially fix the position of the dock member 10 on the carrier tray 12 when coupled thereto. However, other suitable mechanisms for substantially fixing the position of the dock member 10 on the carrier tray 12 can be used. The dock member 10 can have a surface that can receive a baby (e.g., newborn baby, premature newborn baby) or infant thereon between a pair of side walls. Additionally, the dock member 10 can have a recess (e.g., circular recess) that at least partially receives the baby's or infant's head therein. Further details of the dock member 10 can be found in U.S. patent application Ser. No. 15/254,766, filed Sep. 1, 2016, the entire contents of which are incorporated by reference and should be considered a part of this specification. In other embodiments, the rocker assembly 100 does not include the dock member 10. In such embodiments, the infant can optionally be placed directly on the carrier tray 12 or another structure on or attached with the carrier tray 12. In implementations where both the dock member 10 and the carrier tray 12 are excluded, the infant can be placed directly on the carrier support 11.

The proximal curved wall 12D of the carrier tray 12 can provide a limit for the distance the baby's or infant's legs can extend to, as well as serve as a support for the baby's or infant's feet, while accommodating babies or infants of varying lengths thereon. Similarly, the proximal curved wall 11D of the carrier support 11 can provide a limit for the distance the baby's or infant's legs can extend to, as well as serve as a support for the baby's or infant's feet. In some embodiments, the carrier tray 12 can be excluded and the baby or infant supported on the carrier support 11 (e.g., with a dock member 10 disposed on the carrier support 11 rather than the carrier tray 12); in such an embodiment, the proximal curved wall 11D can be movably adjustable relative to the distal end of the carrier support 11 to adjust the length of the carrier support 11 to accommodate babies and infants of different sizes on the carrier support 11. In other embodiments, the carrier support 11 can be used for other purposes than supporting thereon a baby or infant in a supine position. For example, in some embodiments, the carrier support 11 can support components that need to be mixed, such as lab equipment (e.g. beakers, test tubes) filled with test samples.

With reference to FIGS. 3-5, the carrier tray 12 can have a length L1 that can be between about 20 and 40 inches, such as about 30 inches. The recess in the dock member 10 can be spaced from the proximal curved wall 12D of the carrier tray 12 by a distance L2, which generally defines the height of the baby or infant that can be supported on the carrier tray 12. In on embodiment, the distance L2 can between about 18 and 40 inches, such as about 22 inches. The carrier tray 12 can have a maximum height H above a support surface of between about 5 and 12 inches, such as about 9 inches. The carrier tray 12 can have a maximum width W1 of between about 10 and about 24 inches such as about 16 inches. The carrier support 11 can have a length that is shorter than the length L1. The base 16 can have a length L3 of between about 8 and 20 inches, such as about 16 inches, and can have a width W2 of between about 8 and 20 inches, such as about 12 inches. However, other suitable dimensions are possible.

The support assembly 30 can advantageously impart motion to the carrier support 11, and optionally to the carrier tray 12 if disposed on the carrier support 11, in various degrees of freedom. As illustrated in FIG. 1, the support assembly 30 can move the carrier assembly 20 in a yaw direction Y about a yaw axis Y1. The yaw axis Y1 can extend through the joint 8 and/or the center of rotation of the motor platform 1. The support assembly 30 can move the carrier assembly 20 in a roll direction R about a roll axis R1. The roll axis R1 can extend through the joint 8. The support assembly 30 can move the carrier assembly 20 in a pitch direction P about a pitch axis P1. The pitch axis P1 can extend through the joint 8. In addition, in some implementations, the support assembly 30 (e.g., the motor assemblies 2A) can vertically move the carrier assembly 20 in an elevation direction E1 relative to the upper yoke 8B, where the upper yoke 8B slides within the central opening 11B as the elevation of the carrier assembly 20 is varied. The plurality of motor assemblies 2A can be disposed circumferentially about the joint 8. The plurality of motor assemblies 2A can control the roll, pitch, and vertical movement using the drive assemblies 5, or any combination of these. Optionally, the motor assemblies 2A can each be controlled independently of each other.

Figure 6:
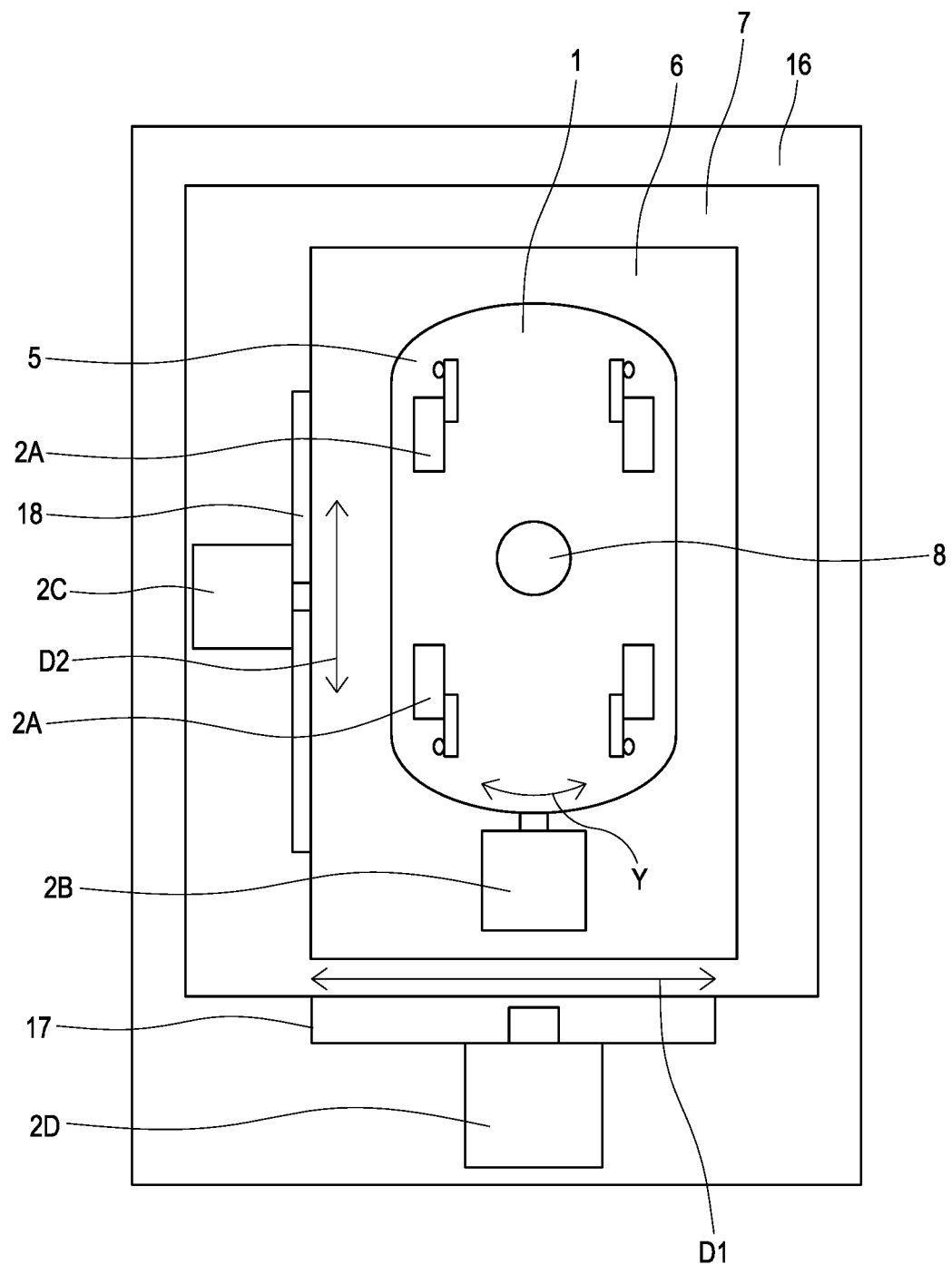
FIG. 6 is a schematic top planar view of the support assembly of FIG. 1.
Figure 7:
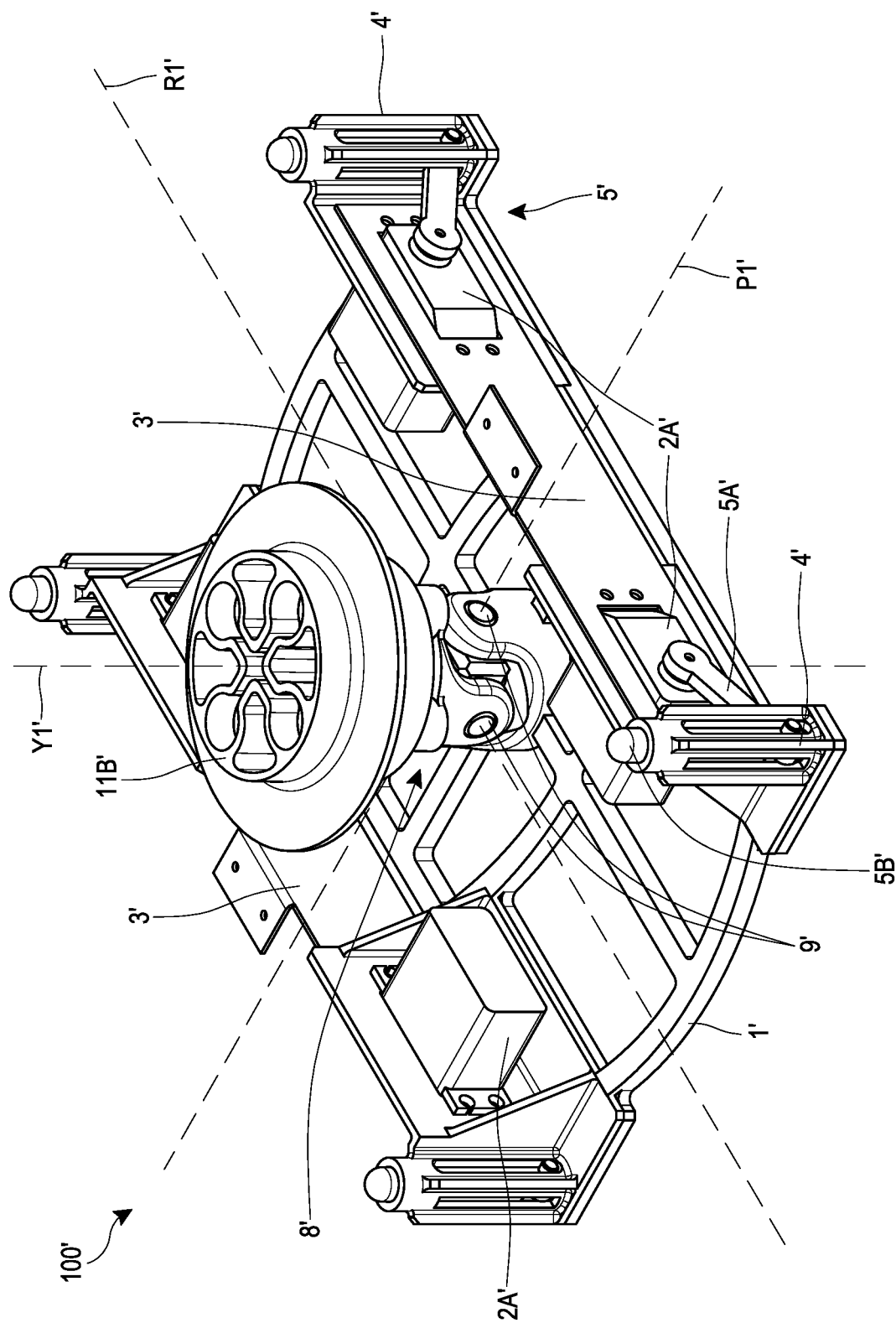
FIG. 7 is a perspective top view of a support assembly of another rocker assembly.

A motor 2B can be coupled with either the motor platform 1 or the second translation platform 6 and provide rotation of the motor platform 1 in the Y direction (e.g., motor 2B includes pinion that engages a rack attached to the motor platform 1, not shown). As illustrated in FIG. 6, the support assembly 30 can impart translation motion in directions D1 and/or D2 to the carrier assembly 20 through the joint 8 (e.g., through the upper yoke 8B). A motor 2C of the plurality of motor assemblies 2 can couple with either the second translation platform 6 or the first translation platform 7 and provide translation of the motor platform 1 in the D2 direction (e.g., motor 2C includes pinion that engages a rack 18). A motor 2D of the plurality of motor assemblies 2 can couple with either the first translation platform 7 or the base 16 and provide translation of the motor platform 1 in the D1 direction (e.g., motor 2D includes pinion that engages a rack 17). Any combination of the above movements can be combined or left out in any implementation.

FIGS. 7-13 show another embodiment of a rocker assembly 100'. The assembly 100' is constructed similar to the rocker assembly 100 shown in FIGS. 1-6, except as noted below. Thus, the reference numerals used to designate the various components of the assembly 100' are generally similar to those used for identifying the corresponding components of the assembly 100 in FIGS. 1-6, except that a "'" has been added to the reference numerals.

The rocker assembly 100' includes a carrier assembly 20' (not shown) supported by a support assembly 30'. The carrier assembly 20' provides support to an infant or other item placed on the carrier assembly 20'. The carrier assembly 20' is at least partially supported by a joint 8' that couples between the carrier assembly 20' and the support assembly 30'. The joint 8' can be a universal joint that allows the carrier assembly to rotate about a roll axis R1' and a pitch axis P1'. The roll axis R1' and the pitch axis P1' can extend through the joint 8' (e.g., through pivot members 9 of the joint 8').

Figure 8:
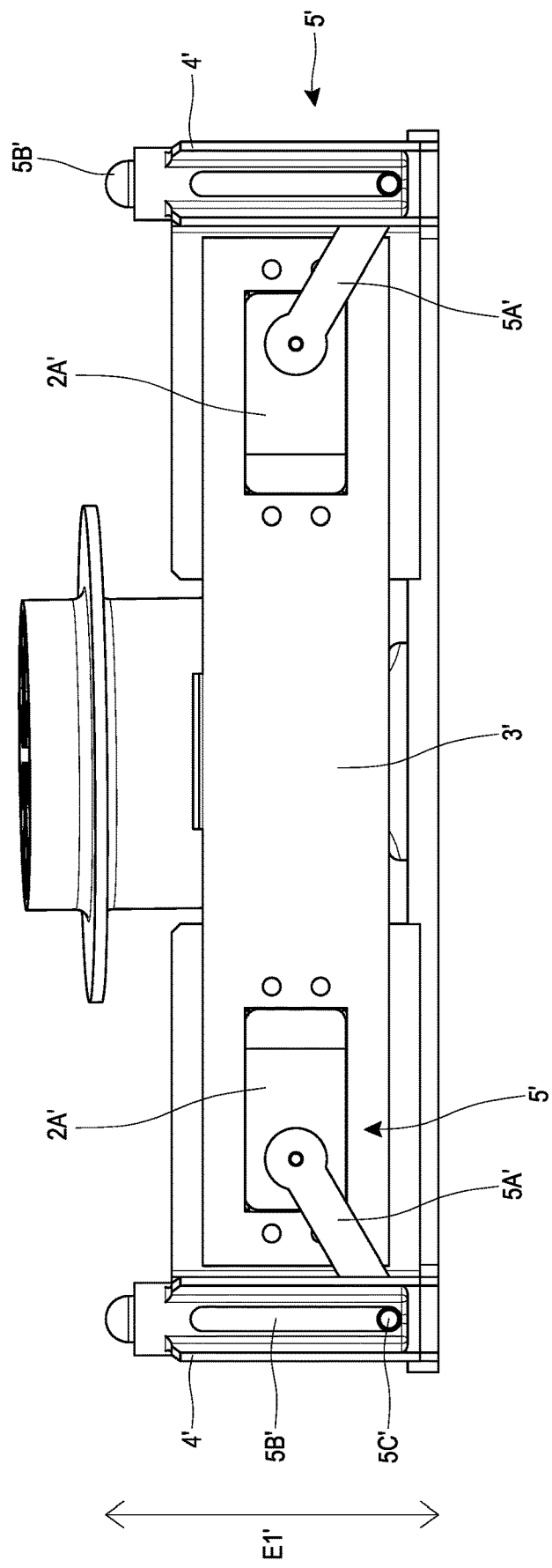
FIG. 8 is a right side view of the rocker assembly of FIG. 7 in a first configuration.
Figure 9:
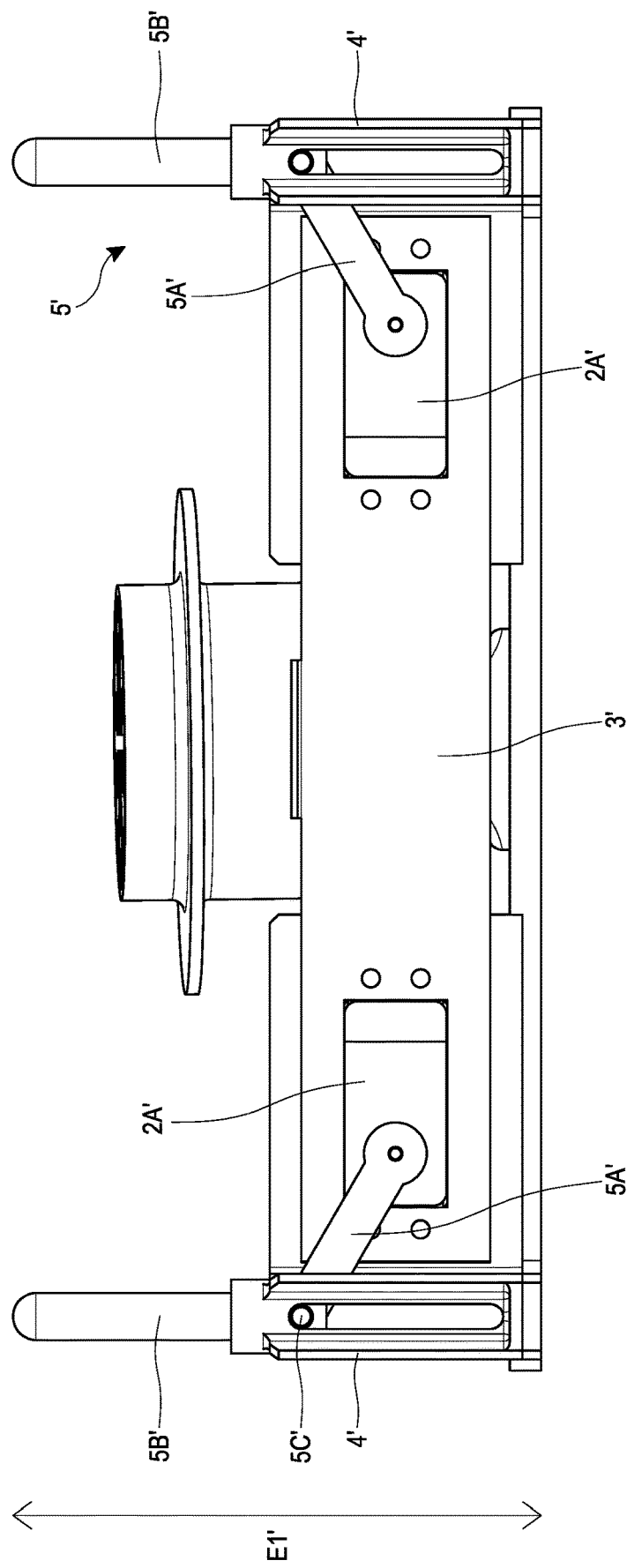
FIG. 9 is a right side view of the rocker assembly of FIG. 7 in a second configuration.

Support assembly 30' includes a frame 1' (similar to motor platform 1) that supports one or more motors 2A' and corresponding drive assemblies 5' (e.g., cam mechanisms). The drive assemblies 5' can include drive arms 5A' pivotably coupled with drive rods 5B'. The drive arms 5A' couple with rotating shafts extending from the motors 2A'. The drive rods 5B' can translate in a vertical direction E1', as shown in FIGS. 8 and 9. The drive rods 5B' can engage (e.g., operatively contact, directly contact) the carrier assembly 20' (e.g., a lower surface of the carrier assembly 20'). The drive assembly 5' that connects each motor 2A' to its corresponding drive rod 5B' can connect via a connector 5C' (e.g., pin or pivot) that enable the driver rods 5B' to translate in vertical direction E1'.

The motors 2A' and the drive assemblies 5' can couple with one or more side supports 3' (e.g., side walls). The side supports 3' can couple with the frame 1'. Optionally, the side supports 3' and the frame 1' form a single piece. In one implementation, the side supports 3' extend generally perpendicularly to the frame 1'. Shafts structures 4' can support the drive rods 5B'. The shaft structures 4' can be formed integrally with the side supports 3', in some implementations. In other implementations, the shaft structures 4' can be formed in an attachable platform (similar to bearing platform 4) that couples with the frame 1'.

The frame 1' is supported by a supporting platform (not shown), which can be similar to (e.g., can include any one or more of) the base 16, the platform 6 and/or the platform 7 previously described in connection with FIGS. 1-6. In some implementations, the frame 1' rotates relative to the supporting structure about a yaw axis Y1'. The yaw axis Y1' can extend through at least a portion of the joint 8' (e.g., through a lower yoke 8A', through a bearing 9', and/or through an upper yoke 8B'). A motor assembly 2B' can provide rotation to the frame 1' about the yaw axis Y1'. For example, the motor assembly 2B' can include a pinion 19A' that engages a rack 19B'. The pinion 19A' couples with either the frame 1' or the supporting structure. The rack 19B' couples with the other one of the frame 1' or the supporting structure.

The carrier assembly 20' can be at least partially supported by the drive assemblies 5'. Each of the motors 2A' optionally can be independently actuated to move the drive assemblies 5'. In another implementation, at least two of the motors 2A' can optionally be actuated simultaneously or in unison. FIG. 8 illustrates the drive assemblies 5' in an extended position and FIG. 9 illustrates the drive assemblies 5' in a lowered position. Through engagement with the underside of the carrier assembly 20', the drive assemblies 5' can provide motion to the carrier assembly 20' (e.g., rotation about the roll and pitch axis R1', P1').

Optionally, the joint 8' can transfer torque between the frame 1' and the carrier assembly 20'. The universal joint 8' can include a lower yoke 8A' that couples with the frame 1'. An upper yoke 8B' of the universal joint can engage the carrier assembly 20'. A universal joint bearing 9' pivotably couples the upper and lower yokes 8A', 8B'. In one implementation, as illustrated in FIGS. 12A-12B, the upper yoke 8B' can have a cross-section with engagement ribs 21' (e.g., cross-shaped with curved or circular ends), which can extend into a correspondingly shaped opening 23' (cross-shaped with circular ends 22') of a coupler 11B'. The coupler 11B' couples with the carrier assembly 20' (e.g., the coupler 11B' can be an integral or assembled component of the carrier assembly 20'). The upper yoke 8B' can engage the coupler 11B' (e.g., the ribs 21' of the upper yoke 8B' can engage the opening 23' of the coupler 11B') in a manner that transfers torque. However, the upper yoke 8B' and opening 23' can have other suitable shapes for transferring torque (e.g., square, rectangular, or other polygonal shapes, etc.). Advantageously, the upper yoke 8B' can readily transfer torque (and motion) about the yaw axis Y1' to the carrier assembly 20' via the engagement of one or more of the engagement ribs 21' with the opening 23', via for example the engagement of the curved or circular surfaces of the ribs 21' with the circular openings 22' of the coupler 11B'.

Additionally, when the carrier assembly 20' is rotated about the pitch axis P1' or uniformly lifted in the vertical direction E1' via extension of one or more of the drive rods 5B', the upper yoke 8B' readily slides in and out of the opening 23' on the underside of carrier assembly 20' to facilitate the vertical motion. Moreover, the universal joint bearings 9' allow the universal joint 8' to pivot when the carrier assembly 20' is moved about the roll and pitch axes R1', P1'. Accordingly, movable engagement of the upper yoke 8B' and coupler 11B' allow the joint 8' to transfer torque to the carrier assembly 20' to rotate the carrier assembly 20' about the yaw axis Y1', while optionally also elevating the carrier assembly 20' relative to the joint 8'.

Figure 13:
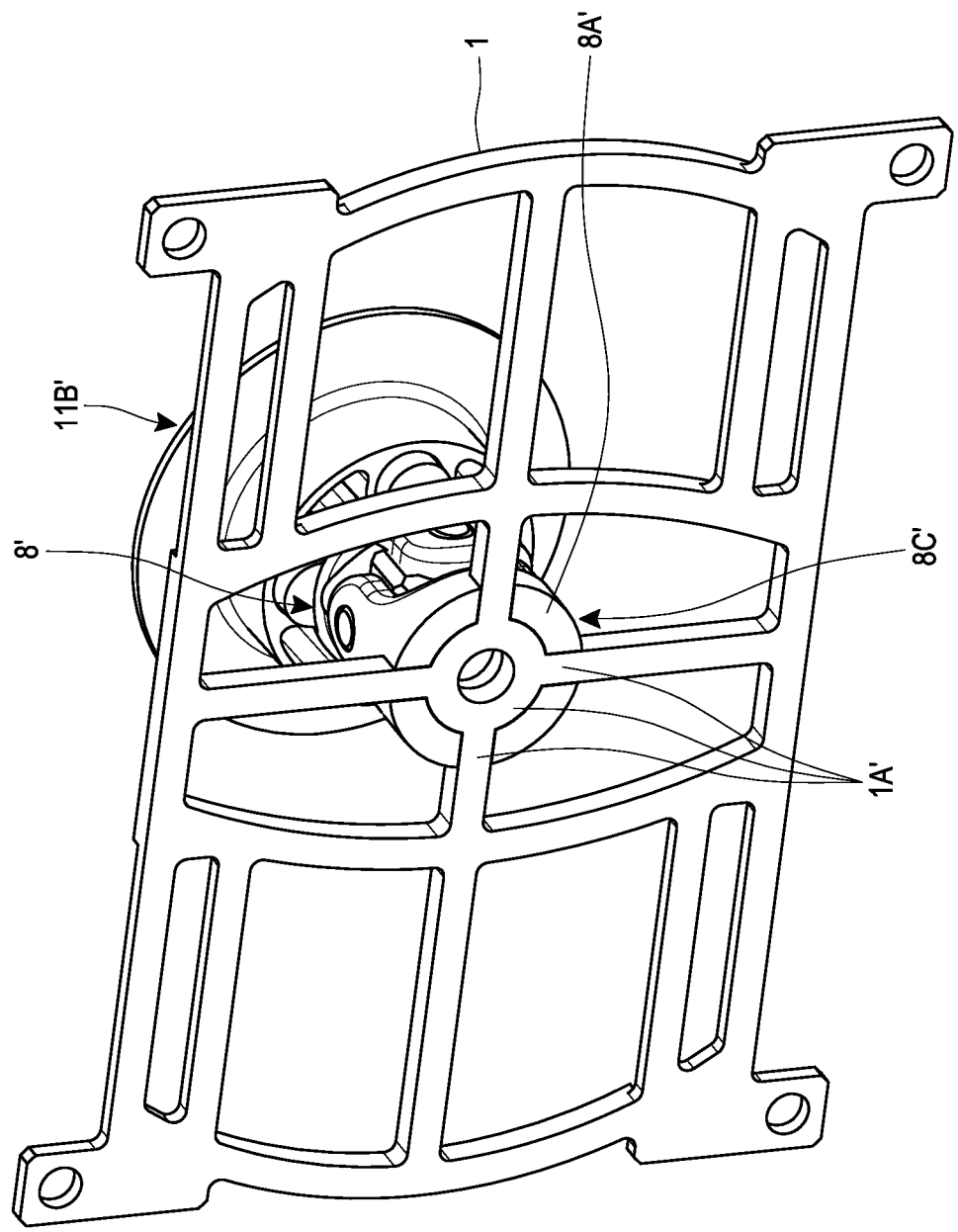
FIG. 13 is a bottom perspective view of the universal joint of FIG. 7, with some elements removed for clarity.

As illustrated in FIG. 13, the lower yoke 8A' can include an engagement feature 8C' for coupling with the frame 1' and effectively transferring torque therebetween. In the illustrated embodiment, the engagement feature 8C' includes one or more notches in a cross shape and engages with members 1A' of the frame 1'. However, the engagement feature 8C' can have other suitable shapes. Additionally or alternatively, the lower yoke 8A' can be coupled to the frame 1' using one or more fasteners (e.g., bolts, screws) that extend through an opening in the frame aligned with a bore (e.g. threaded bore) in the portion of the lower yoke 8A' that engages the frame 1'.

Figure 10:
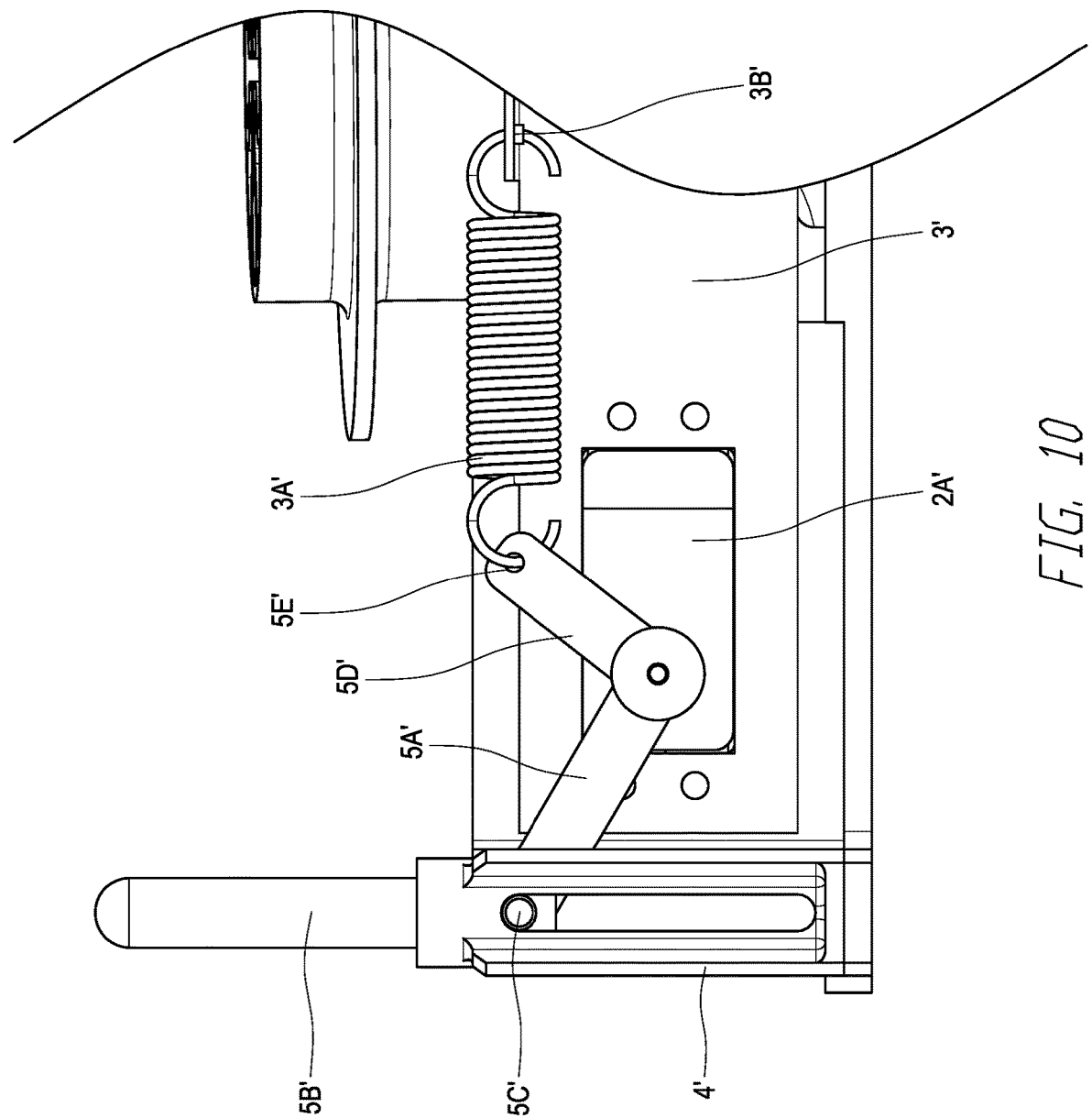
FIG. 10 is a partial right side view of a section of the rocker assembly of FIG. 7.
Figure 11:
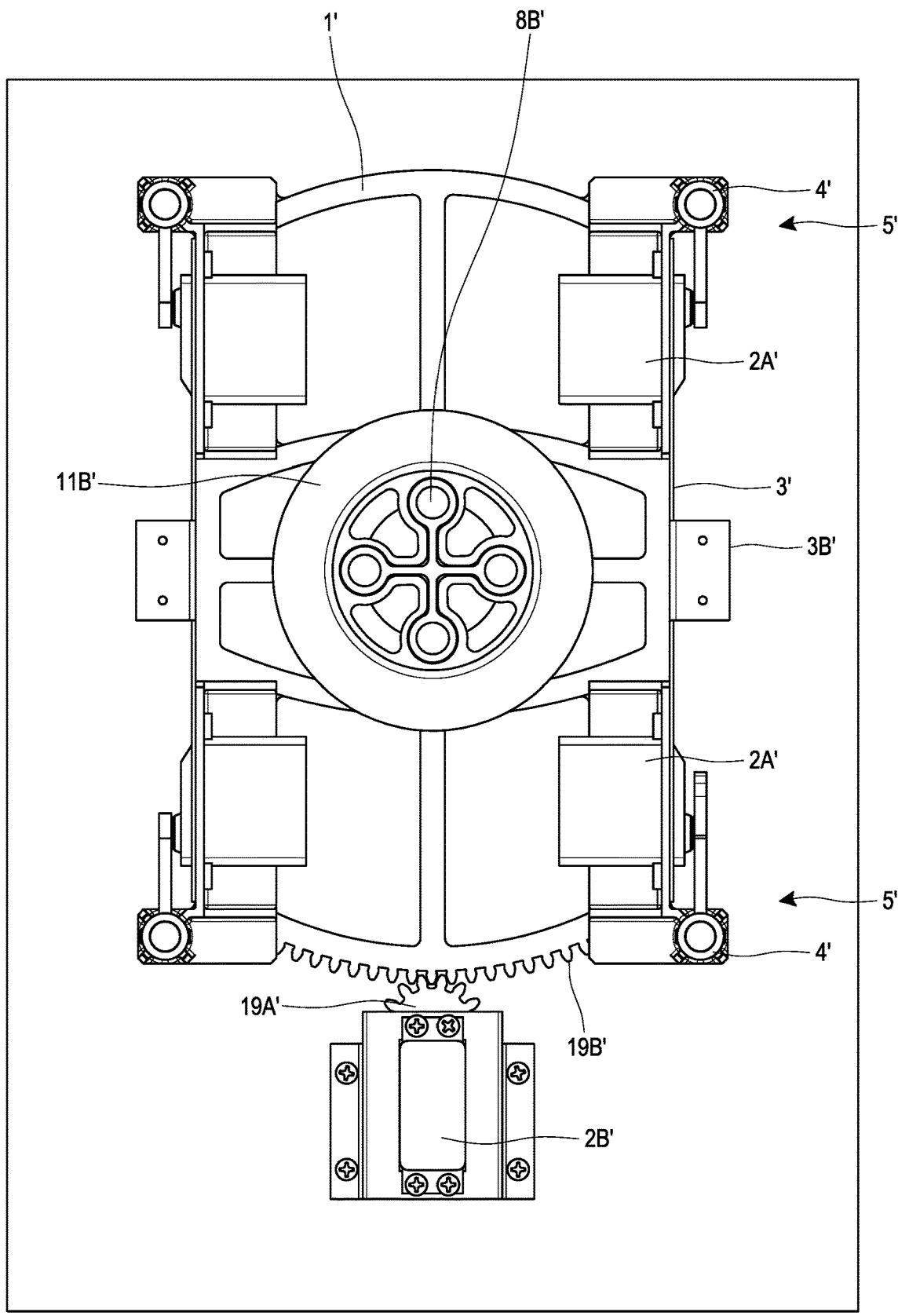
FIG. 11 is a top planar view of the support assembly of FIG. 7.

With reference to FIG. 10, the drive arm 5A' optionally couples to the motor 2A' (e.g., couples to an output shaft of the motor 2A') at a proximal end of the drive arm 5A'. In some implementations, the drive arm 5A' also couples with or includes a support member 5D'. The support member 5D', as illustrated in FIG. 13 can create an L-shape with the drive arm 5A', in other embodiments the support member 5D' can form cross, circle, or any other suitable shapes. The drive arm assembly 5' can include an elastic member 3A' (e.g., spring, such as a coil spring). The elastic member 3A' can be coupled on one end to the side support 3' at coupling location 3B'. In some implementations, the coupling location 3B' can be an extension of the side support 3'. Another end of the elastic member 3A' can be coupled with the support member 5D' at a coupler 5E'. In one implementation, the coupler 5E' and/or the coupling location 3B' can include holes for receiving ends of the elastic member 3A'.

The elastic member 3A' applies a tension force (e.g., creating a moment on the drive arm 5A' and/or the rotating shaft of the motor 2A') on the support member 5D', which can help support a load on the drive rod 5B' due to the weight of the carrier assembly 20'. This can reduce the work performed by (and the power requirements of) the motors 2A' during operation of the rocker assembly 100' (e.g., because some of the weight on the carrier assembly 20' is offset by the elastic member 3A' during lifting of the drive arm 5B'. This can advantageously improve the effective working life of the power supply (e.g., batteries) and the motors 2A'. In one implementation, the tension capacity of the elastic member 3A' and/or lengths and proportions of the drive arm 5A'/5D' can be tuned to accommodate a specific range or weights placed on the carrier assembly 20' (e.g., the tension of the elastic member 3A' can be matched based on the weight placed on the carrier assembly 20'). For example, the rocker assembly 100' can be tuned to support a weight corresponding to the weight of an infant (e.g., between 3 and 12 lbs.).

The rocker assembly 100' can be powered with a power supply PS'. In the illustrated embodiment, the power supply PS' can be one or more batteries (e.g., LiPo batteries), which can optionally be rechargeable. The power supply PS' can be housed in the body of the rocker assembly 100' or can optionally be separately coupled to the rocker assembly 100' via an electrical connector (not shown), which can optionally be a USB connector, micro-USB connector, etc.

In the illustrated embodiment, the rocker assembly 100' includes the one or more motors 2A' (e.g., servo or electric motors) that move corresponding the drive rods 5B' via interconnected drive arm assemblies 5A'. In another embodiment, the drive assembly 5' can instead include a gear train (or other camming device) between the one or more motors 2A' and corresponding drive rods 5B' to effect movement of the drive rods 5B'. In one embodiment, the one or more motors 2A' can include attached gears. In another implementation, the rocker assembly 100, 100' includes a pneumatic system (e.g., gas reservoir, one or more valves) for actuating the movement of the drive rods 5B, 5B'. For example, each motor 2A, 2A' can drive a piston that travels within a conduit filled with a gas (e.g., air) in fluid communication with a base of one of the drive rods 5B, 5B', and the drive rods 5B, 5B' can travel up and down based on the movement of the piston (forward or rearward) that is effected by the motor 2A, 2A'. In another implementation, the rocker assembly 100, 100' includes a hydraulic system (e.g., one or more pumps, one or more valves) for actuating the movement of the drive rods 5B, 5B'. For example, each motor 2A, 2A' can drive a piston that travels within a conduit filled with a liquid (e.g., water) in fluid communication with a base of one of the drive rods 5B, 5B', and the drive rods 5B, 5B' can travel up and down based on the movement of the piston (forward or rearward) that is effected by the motor 2A, 2A'.

Figure 14:
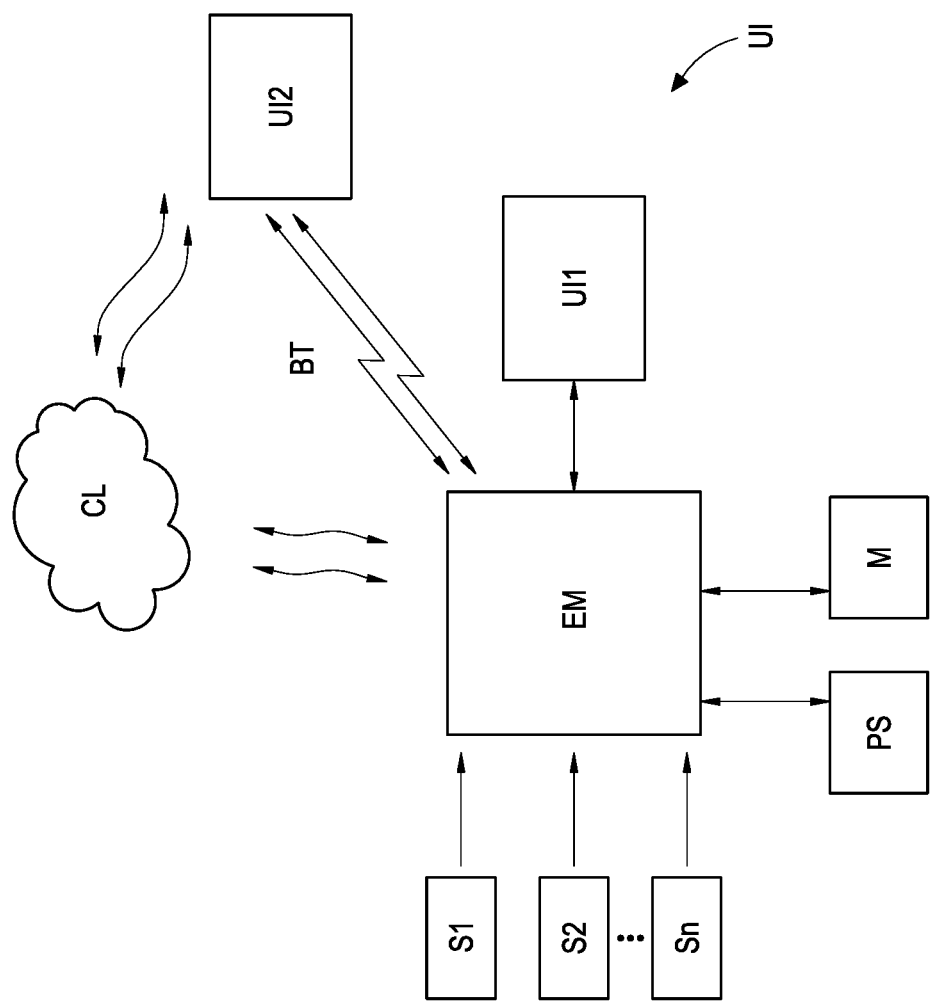
FIG. 14 is a schematic view of a control system for the rocker assemblies of FIG. 1 or FIG. 7.

With reference to FIG. 14, the motion imparted by the rocker assembly 100, 100' can be controlled by a controller UI, as further discussed below. The controller UI can be incorporated into the rocker assembly 100, 100'. Alternatively, the controller UI can be a separate unit that connects (e.g., removably connects) to electronics of the rocker assembly 100, 100' (e.g., via an electrical connector). One or more motions or motion patterns can be programmed into the controller UI (e.g., by the user, at the factory during manufacture) so that the user can simply select the type of motion or motion pattern they desire via a user interface, where the user interface can communicate such instructions to electronic control circuitry EM of the controller UI to actuate the one or more motors M of the rocker assembly 100 to effect the desired motion. Optionally, the controller UI can include a user interface UI1 that has a hardwire connection to the circuitry EM. For example, the user interface UI1 can be disposed on a surface of the rocker assembly 100. Additionally or alternatively, a remote user interface UI2 (i.e., not mounted on a surface of the rocker assembly 100, 100') can communicate wirelessly with the control circuitry EM of the control circuitry EM (e.g., via radiofrequency (RF) communication BT using a transceiver or receiver on control circuitry EM that communicates with a transceiver or transmitter in the remote user interface UI2).

In one embodiment, the motion effected by the rocker assembly 100, 100' (via the one or more motors M) can be computer controlled (e.g., controlled from a remote electronic device such as a computer, tablet computer, laptop computer, smartphone, electronic wearable device, etc.), such as via the remote user interface UI2. Optionally, the motion effected by the rocker assembly 100, 100' can be controlled (by the controller UI) to generate soft start and stop motions that gradually increase (at start) and decrease (at end) in amplitude (e.g., to a programmed or user selected value), so as to advantageously avoid sudden motion or jolts (e.g., that may disturb or wake the baby or infant).

In one embodiment, the remote user interface UI2 can be part of a remote electronic device, such as a smartphone, tablet computer, electronic wearable device that transmits (e.g., wirelessly transmits, such as using BLUETOOTH®) instructions (e.g., motion pattern) to the control circuitry EM, such as via a mobile app installed in the remote electronic device. In another embodiment, the remote user interface UI2 can communicate wirelessly with the control circuitry EM via the internet CL. In one embodiment, communication between the user interface UI1, UI2 and the control circuitry EM can be one-way communication (e.g., the user interface UI1, UI2 can provide instructions to the control circuitry EM but does not receive any information from the control circuitry EM), or vice-versa (i.e., where the remote user interface UI2 can receive one or more alert signals but does not send any information to the control circuitry EM). In another embodiment, communication between the user interface UI1, UI2 and the control circuitry EM (e.g., integrated into the rocker assembly 100, 100') can be two-way communication (e.g., the user interface UI1/UI2 can provide instructions to the control circuitry EM, as well as receive information from the control circuitry EM). For example, the user interface UI1, UI2 can receive a signal from the control circuitry EM when motion of the rocker assembly 100 has terminated. In another embodiment, the user interface UI1, UI2 can receive a signal from the control circuitry EM when the charge level of one or more batteries PS is below a threshold amount, when the presence of weight (e.g., lab equipment, infant, etc.) is sensed on the rocker assembly 100, 100', when the baby or infant on the rocker assembly 100 has awoken, as further discussed below.

In one embodiment, motion of the remote electronic device (e.g., smartphone) by the user can effect motion of the rocker assembly 100, 100' in substantially the same manner. For example, the accelerometer data from the user moving the remote electronic device (e.g., in a rocking manner) can be transmitted via the remote user interface UI2 to the control circuitry EM to effect motion of the rocker assembly 100, 100' (via the one or more motors M) in a motion pattern that substantially corresponds to the accelerometer data.

The rocker assembly 100, 100' can have one or more sensors S1-Sn that can communicate with the control circuitry EM. Optionally, the control circuitry EM can operate the rocker assembly 100, 100' based at least in part on a signal from the one or more sensors S1-Sn and/or communicate information with the user interface UI1, UI2 based on said signal from the one or more sensors S1-Sn. In one embodiment, the one or more sensors S1-Sn can include one or more position sensors that communicate a position of the one or more drive rods 5B to the control circuitry EM, which allows the control circuitry EM to determine the position (e.g., in yaw, pitch, roll and/or elevation) of the carrier support 11. The one or more position sensors optionally can be disposed on the drive rod 5B, 5B', drive arm 5A, 5A' or motor 2A, 2A' (e.g., output shaft of motor). Such position sensors can be encoders on the motors, servos, transducers, hall-effect sensors, etc.

In one embodiment, the one or more sensors S1-Sn can include a load sensor that can sense when weight is placed on the carrier support 11 (e.g., when lab equipment such as beakers or test tubes are placed on the carrier support 11, when a baby or infant is placed on the carrier support 11, etc.). The control circuitry EM can in one embodiment (e.g., automatically) initiate operation of the one or more motors M (such as the motor assemblies 2) to effect movement of the carrier support 11 in one or more directions only when the control circuitry EM receives a signal from the load sensor indicating a weight has been placed on the carrier support 11 (e.g., when the load sensor senses a weight above a predetermined threshold, due to placement of an infant on the carrier support 11, due to placement of lab equipment on the carrier support 11, etc.). In one embodiment, the control circuitry EM can communicate a signal to the user interface UI (e.g., to the remote user interface UI2) to alert the user when the weight has been placed on the rocker assembly 100, 100' and/or when the weight has been removed from the rocker assembly 100, 100'. In this manner, a user (e.g., parent) can receive an alert signal indicating when the baby or infant is no longer on the rocker assembly 100, 100' (e.g., because the nanny or baby sitter has picked up the baby or infant if they awoke and/or were crying) and the parent can determine whether to check on the baby or infant. In one embodiment (as discussed further below), the alert signal can be a silent alert signal (e.g., vibration), for example communicated wirelessly to a smartphone or wearable device (e.g., wristband) so as not to alert or disturb more persons than necessary.

Additionally or alternatively, the one or more sensors S1-Sn can include a motion sensor (e.g., an accelerometer, such as a three-axis accelerometer) that can sense motion of a portion of the rocker assembly 100, 100' (e.g., motion of the carrier support 11). The control circuitry EM can in one embodiment (e.g., automatically) initiate operation of the one or more motors M (such as the motors 2) to effect movement of the carrier support 11 in one or more directions when the control circuitry EM receives a signal from the motion sensor indicating motion on the carrier support 11 (e.g., if the baby or infant disposed on the carrier support 11, such as on the dock member 10, is waking up and moving). In one embodiment, the control circuitry EM can communicate a signal to the user interface UI1, UI2 to alert the user when the motion sensor senses motion (e.g., indicating the baby or infant on the rocker assembly 100 may be waking up). In this manner, a user (e.g., parent) can receive an alert signal indicating when the baby or infant on the rocker assembly 100, 100' may be waking up and the parent can determine whether to check on the baby or infant, or can operate the user interface UI1, UI2 to send instructions to the control circuitry EM to carry out one or more programmed motions on the carrier support 11 (e.g., to rock the baby or infant back to sleep). In one embodiment, the alert signal can be a silent alert (e.g., vibration) on a smartphone or wearable device so as not to alert or disturb more persons than necessary.

Additionally or alternatively, the one or more sensors S1-Sn can include a sound sensor (e.g., a microphone) that can sense sound. The control circuitry EM can in one embodiment (e.g., automatically) initiate operation of the one or more motors M (such as the motors 2) to effect movement of the carrier support 11 in one or more directions when the control circuitry EM receives a signal from the sound sensor indicating the baby or infant on the rocker assembly 100, 100' may be waking up or crying (e.g., if the sensed sound is above a predetermined decibel level). In one embodiment, the control circuitry EM can communicate a signal to the user interface UI1, UI2 to alert the user when the motion sensor senses sound (e.g., indicating the baby or infant on the rocker assembly 100, 100' may be waking up or crying); in another embodiment, the control circuitry EM can transmit the sensed sound to the user interface UI1, UI2 (e.g., a speaker of the user interface UI1, a speaker of the remote electronic device that includes the remote user interface UI2) for the user to hear. In this manner, a user (e.g., parent) can receive an alert signal indicating when the baby or infant on the rocker assembly 100, 100' may be waking up, and/or can receive the sensed sound itself, and the parent can determine whether to check on the baby or infant, or can operate the user interface UI1, UI2 to send instructions to the control circuitry EM to carry out one or more programmed motions on the carrier support 11 (e.g., to rock the baby or infant back to sleep). In one embodiment, the alert signal can be a silent alert (e.g., vibration) on a smartphone or wearable device so as not to alert or disturb more persons than necessary.

Figure 15:
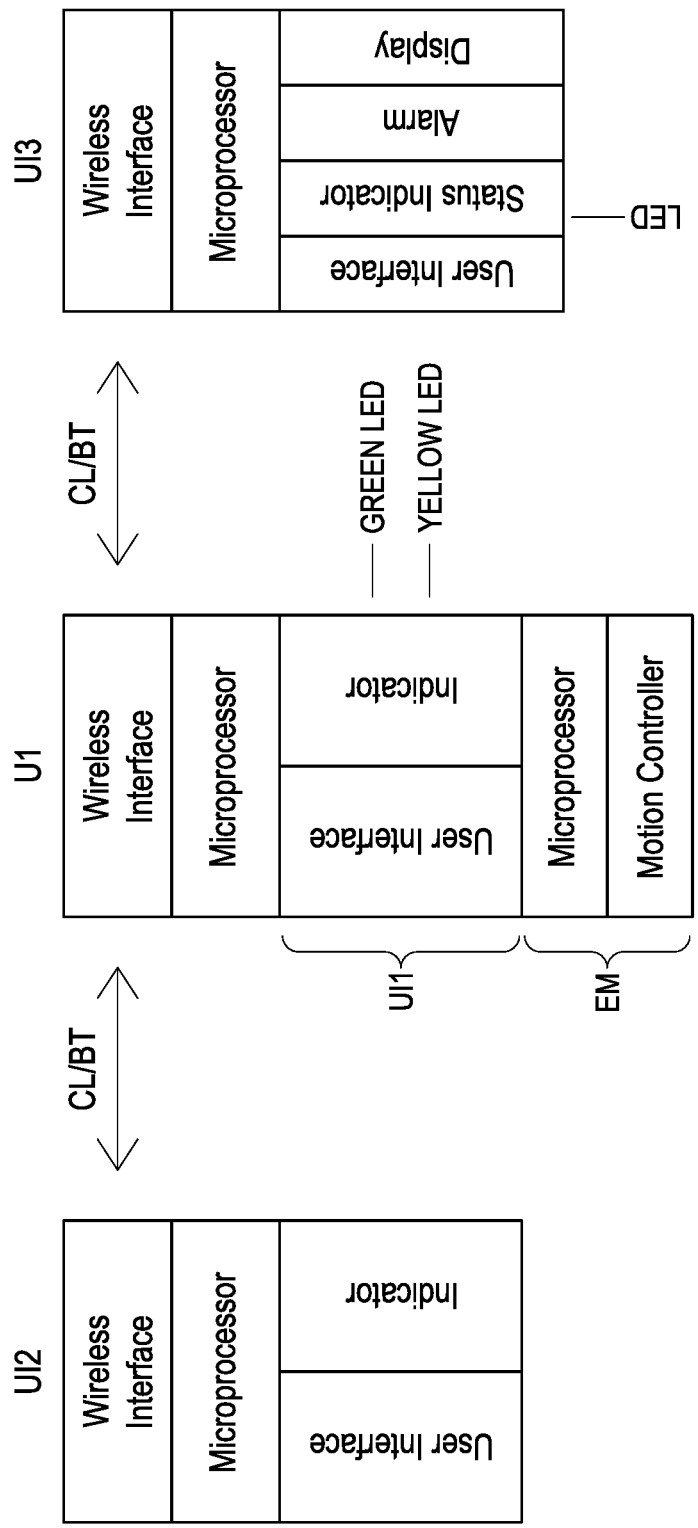
FIG. 15 is a schematic view of control modules for the control system of FIG. 14.

FIG. 15 illustrates embodiments of the controller UI, which can be implemented with the rocker assembly 100, 100'. The user interface UI1 is optionally integrated with or hardwired in connection with the control circuitry EM. The user interface UI1 can include a user interface (e.g., a keypad or touchscreen) for allowing the user to input a command (e.g., motion pattern, start/stop) to the control circuitry EM. A microprocessor of the controller UI operates to process the input commands and to send a signal to effect the motion pattern contained in the instructions to the control circuitry EM (e.g., a motion controller of the motors 2). The control circuitry EM can operate the motors of the rocker assemblies 100, 100' to effect the selected motion pattern. The user interface UI1 can include an indicator (e.g., status LEDs) corresponding to the status of the control circuitry EM.

The controller UI (optionally the control circuitry EM or the user interface UI1) can include a wireless interface for wirelessly receiving (e.g., via RF communication BT or internet CL) transmitted instructions (e.g., user input, motion patterns, etc.) from the remote user interface UI2 and/or a remote alarm UI3. The remote user interface UI2 and the remote alarm UI3 can similarly include wireless interfaces in communication with the controller UI. The user interface of any or all of the user interface UI1, remote user interface UI2, or remote alarm UI3 can include one or more indicators (e.g., status LEDs) corresponding to the status of the control circuitry EM (e.g., on/off). The one or more indicators can also indicate the status of the wireless connection with the other user interface components UI1, UI2, UI3.

The remote user interface UI2 can include a user interface, such as a keypad, or touchscreen, for inputting a command. The remote user interface UI2 can be integrated into a remote or mobile electronic device (e.g., smartphone, tablet computer, wearable device). A microprocessor on the remote user interface UI2 can process the input command from the user interface. The wireless interface on the remote user interface UI2 can transmit instructions corresponding to the input command to the controller UI. Similarly, the remote alarm UI3 can include a user interface, such as a keypad, or touchscreen, for inputting a command. A microprocessor on the remote electronic device UI2 can process the input command from the user interface. The wireless interface on the remote user interface UI2 can transmit instructions corresponding to the input command to the controller UI. The controller UI can process the transmitted instructions with its microprocessor, as explained above.

In some implementations, the remote alarm UI3 can be used as an alarm system (e.g., vibrating wristband, smart device, phone or the like) for alerting a user (e.g., a caretaker of the rocker assembly 100 or infant) when one of the sensors S1-Sn detects a situation that requires the attention of the user. In some implementations, the remote user interface UI2 can be combined with the remote alarm UI3 (e.g., the components and/or the functionality of the remote user interface UI2 can be combined with the remote alarm UI3). Exemplary situations are discussed above in reference to the sensors S1-Sn and further discussed below in reference to the situation detection algorithms operated by the control circuitry EM. During an alert, the control circuitry EM can send a signal via the wireless interface of the controller UI to the remote alarm UI3. The wireless interface for communicating with the control circuitry EM on the remote alarm UI3 can receive the signal. The microcontroller of the remote alarm UI3 can process the signal, which can include sending a signal to generate an alarm on the remote alarm UI3. The alarm can be an audible alarm (e.g., a small speaker emitting a sound), a visual alarm (e.g., LED indicators changing status, a green LED can indicate no alarm, a yellow LED and/or a flashing or blinking light can indicate the presence of an alarm signal), or a tactile alarm (e.g., the remote alarm UI3 can include a vibration generator such as a small electric motor with an eccentric weight attached to a rotor). In some embodiments the alarm system could include a message on a display of the remote alarm UI3 indicating the alarm or type of alarm or other status of the rocker assembly 100. In some embodiments, the user interface of the remote alarm UI3 can be used for acknowledging, ignoring, silencing, resetting, arming, sleeping, snoozing or turning off the alarm. In other embodiments, actions by the user to respond to the alarm can only be operated on the controller UI (e.g., user interface UI1). Such a system requires that the user monitor the actual state of the rocker assembly 100.

Figure 16:
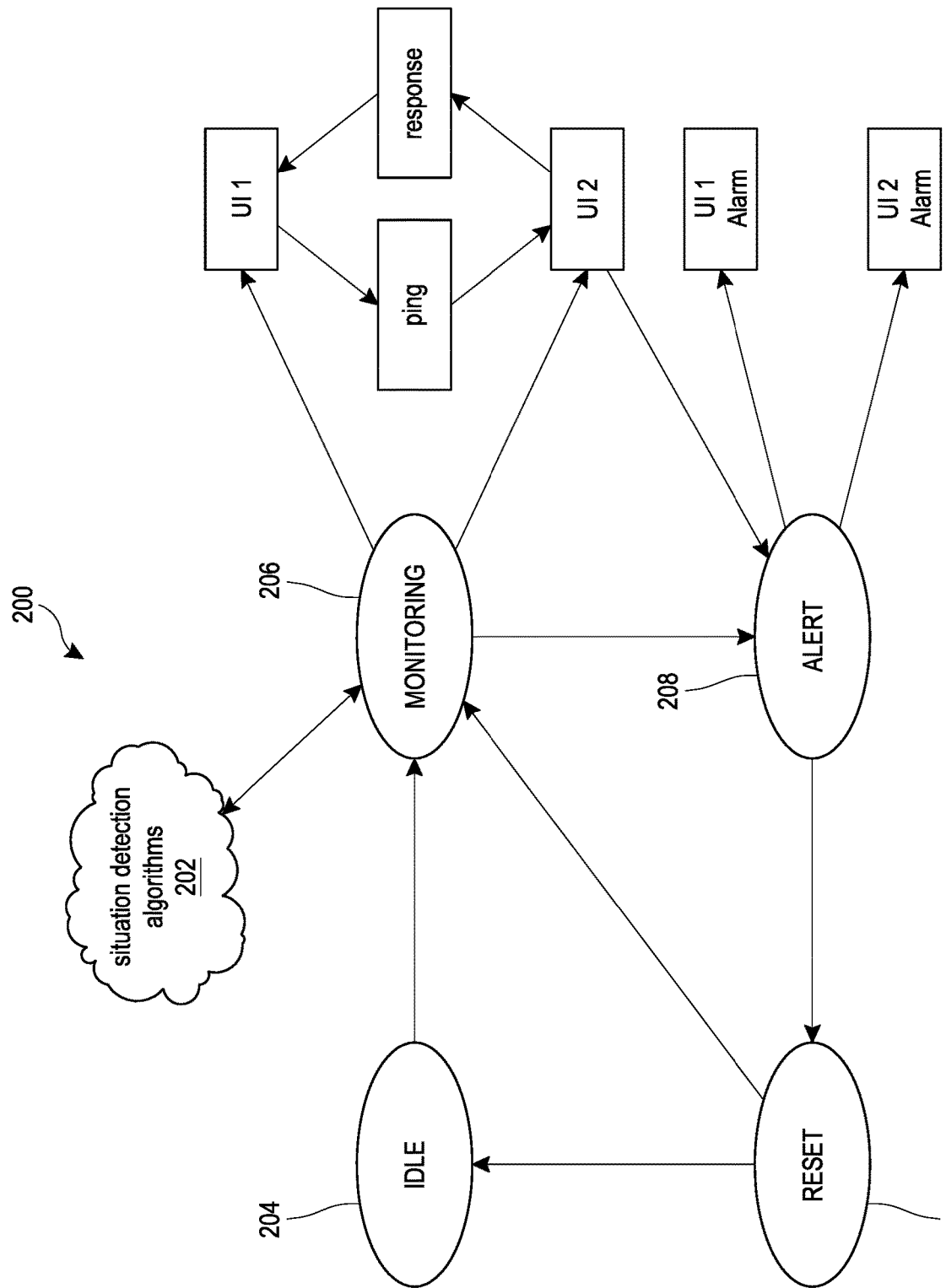
FIG. 16 is a block diagram of an alert algorithm for the control system of FIG. 14.

FIG. 16 illustrates a monitoring algorithm 200. The monitoring algorithm 200 can be operated by the control circuitry EM, as described in FIGS. 14 and 15. The monitoring algorithm 200 can be used as a monitoring and alert system to warn or advise the user (e.g., caretaker) of a problem with the operation of the rocker assembly 100 or various other circumstances as defined in situation detection algorithms 202.

The monitoring algorithm 200 is optionally implemented by one or more microprocessors of the control circuitry EM and can begin in an idle state 204. In the idle state 204, the control circuitry EM can conserve power and await a signal to move out of the idle state 204. The control circuitry EM is generally not operating the motion pattern when in the idle state 204. The control circuitry EM can end the idle state 204 and begin monitoring state 206. In some implementations, idle state 204 can ended automatically (e.g., input from one or more of the sensors S1-Sn). For example, where the rocker assembly 100 includes a weight sensor S1, the idle state 204 can end based on a weight being placed on the carrier support 20. In other implementations, the idle state 204 can end based on input from a user, such as an input command (e.g., motion pattern) through user interfaces of controllers UI1, UI2, UI3. In some implementations, the monitor state 206 can being automatically after the idle state 204 ends.

During the monitoring state 206, the control circuitry EM can monitor the rocker assembly 100 using one or more of situation detection algorithms 202. Upon receipt of a signal from the one or more sensors S1-Sn and/or other outputs from running the situation detection algorithms 202, the control circuitry EM can transition to an alert state 208.

The situation detection algorithms 202 operated during the monitor state 206 can utilize one or more of the sensors S1-Sn of the control circuitry EM. According to a first situation detection algorithm 202, one or more sensors S1-Sn is an accelerometer attached to the rocker assembly 100. The control circuitry EM can receive a signal form the accelerometer indicating or detecting movement of an awake infant on the rocker assembly 100. According to another situation detection algorithm 202, one or more sensors S1-Sn is a microphone. The control circuitry EM receives a signal form the microphone and can execute algorithms that correlate that sound pattern to one indicative of an awake and crying child on the rocker assembly 100. According to another situation detection algorithm 202, one or more sensors S1-Sn is a position or movement sensor (e.g., hall-effect sensor, encoder) on the rocker assembly 100. The control circuitry EM receives a signal form the position or motion sensor and can execute algorithms that correlate the position or motion to an operational, overload, or malfunction situations of the mechanisms or software of the rocker assembly 100. According to another situation detection algorithm 202, one or more sensors S1-Sn is a heart-rate sensor (e.g., hall-effect sensor, encoder) on the rocker assembly 100. The control circuitry EM receives a signal form the heart-rate sensor and can execute algorithms that monitor the heart rate (e.g., ensure heart rate is between specified high and/or low thresholds) of an infant on the rocker assembly 100. According to another situation detection algorithm 202, one or more sensors S1-Sn is a respiration sensor (e.g., hall-effect sensor, encoder) on the rocker assembly 100. The control circuitry EM receives a signal form the respiration sensor and can execute algorithms that monitor the respiration (e.g., ensure respiration rate is between specified high and/or low thresholds) of an infant on the rocker assembly 100. The situation detection algorithms 202 can also be optionally operated automatically with the control circuity EM (e.g., power on) or turned on based on a trigger (e.g., manually through a user interface, or detection by the control circuitry EM of the presence of a peripheral device, such as a heart rate monitor or reparation monitor, or the input of a sensors S1-Sn). According to another situation detection algorithm 202, the control circuitry EM can periodically check on the connection status of the RF communication BT between the controller UI and the remote alarm U13. Where a response is not returned, the control circuitry EM can automatically be transitioned into the alert state 208.

In the alert state 208, the control circuitry EM sends a signal to alert a user of the rocker assembly 100 (e.g., through the remote alarm UI3) that a situation has occurred that requires the attention of the user. In response, the user can reset the alarm and/or respond to the alarm using one of the various user interfaces UI. The reset command can optionally cause the control circuitry EM to enter the reset state 210. From the reset state 210, the control circuitry EM can optionally return to the idle state 204 (and await a signal to transition to the monitor state 206) or the control circuitry EM can return directly to the monitoring state 206.

While certain embodiments of the inventions have been described, these embodiments have been presented by way of example only and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the rocker need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed rockers.

The invention claimed is:

1. An infant rocking system, comprising:
a carrier assembly configured to support an infant thereon, the carrier assembly comprising a support platform having a generally planar top surface and an opening on a bottom surface of the support platform;
a support assembly disposed below the carrier assembly and configured for placement on a planar surface, the support assembly configured to impart motion to the carrier assembly in one or more of rotation about a first axis that extends through the opening, translation along a first linear direction, translation along a second linear direction perpendicular to the first linear direction, yaw relative to the axis, pitch relative to a second axis that is perpendicular to the first axis and roll about a third axis that is perpendicular to the first and second axes, elevation above the support assembly, the support assembly comprising:
a base platform,
a frame movably disposed on the base platform and operable to provide said rotation about the first axis,
a universal joint having a lower yoke fixedly mounted on the frame and an upper yoke slideably coupled within the opening, the upper yoke configured to engage the opening to impart said rotation about the first axis to the carrier assembly based on rotation of the frame,
a plurality of motor assemblies mounted on the frame and arranged circumferentially about the universal joint, each of the motor assemblies configured to engage a different portion of the bottom surface of the support platform and being actuatable independently of each other to impart pitch, roll, and vertical motion to the carrier assembly, each of the motor assemblies comprising:
an electric motor operable to rotate a rotor extending therefrom,
a drive arm coupled with the rotor, and
a drive shaft coupled with the drive arm, the drive shaft configured to translate vertically between the frame and the support platform, a vertical position of the drive shaft controlled by the position of the rotor of the motor, an upper end of the drive shaft configured to engage the bottom surface of the support platform; and
an electronic controller unit operable to control an operation of the plurality of motor assemblies to impart the pitch, roll, and vertical motion on the support platform.

2. The baby rocker of claim 1, further comprising a motor assembly mounted on the base platform and configured to operatively engage the frame and to rotate about the first axis;
the motor assembly comprising a pinion that engages a rack on the frame to effect rotation;
the electronic controller unit operable to control operation of the motor assembly to rotate the frame.

3. The baby rocker of claim 1, wherein the base platform is mounted on a second platform, a motor assembly mounted on the second platform and configured to operatively engage the base platform to translate in the first linear direction relative to the second platform;
the motor assembly comprising a pinion that engages a rack on the base to effect translation;
the electronic controller unit operable to control operation of the motor assembly to translate the base in the first linear direction.

4. The baby rocker of claim 3, wherein the second platform is mounted on a third platform, a motor assembly mounted on the third platform and configured to operatively engage the second platform to translate in the second linear direction relative to the third platform;
the motor assembly comprising a pinion that engages a rack on the second platform to effect translation;
the electronic controller unit operable to control operation of the motor assembly to translate the base in the second linear direction.

5. The baby rocker of claim 1, wherein the electronic controller unit comprises:
a circuitry for controlling motion of the carrier assembly, the control circuit comprising a user interface for inputting a motion pattern;
the circuitry configured to control the operation of the plurality of motors assemblies based on the motion pattern input at the user interface to impart said motion pattern on the carrier support.

6. The baby rocker of claim 5, further comprising:
one or more sensors configured to communicate with the circuitry, the one or more sensors configured to sense one or more of 1) a sound, 3) a movement of the carrier assembly, 3) a heart rate of an infant on the carrier support, and 4) a respiration pattern of the infant;
the circuitry configured to operate the plurality of motors based as least in part on said signals.

7. The baby rocker of claim 6, wherein the circuitry includes a transceiver configured to communicate with a remote electronic device;
the transceiver configured to perform at least one of 1) transmit sensed information to the remote electronic device and 2) receive instructions from the remote electronic device.

8. The baby rocker of claim 7, wherein the circuitry wirelessly receives instructions corresponding to the motion pattern from a user via the remote electronic device.

9. The baby rocker of claim 8, wherein the alarm includes at least one of an audible alarm, a visual alarm and a tactile alarm.

10. The baby rocker of claim 9, wherein the remote electronic device is a wristband configured to be worn by a user, the wristband having a receiver configured to receive the alert signal from the transceiver.

11. The baby rocker of claim 7, wherein the circuitry is configured to generate an alert signal based on the signal from the sensor, the circuitry configured to wirelessly communicate the alert signal with the transceiver to the remote electronic device, the remote electronic device configured to produce an alarm based on the alert signal.

12. The baby rocker of claim 1, further comprising a spring mounted on frame, the spring coupled between the frame and the drive arm and configured to exert a moment on the drive arm and the rotor, the moment opposite to a second moment on the drive arm and rotor from a weight exerted on the drive shaft by the carrier support.

13. The baby rocker of claim 1, wherein a shape of the upper yoke allows it to impart rotation from the lower yoke to the carrier support while also allowing sliding of the carrier support on the upper yoke to effect elevation changes.

14. The baby rocker of claim 1, wherein the carrier assembly further comprises a carrier tray with a proximal curved wall to keep the infant from sliding distally on the carrier assembly.

15. A rocker comprising:
a carrier assembly comprising a support platform and an opening on a bottom surface of the support platform;
a support assembly disposed below the carrier assembly and configured for placement on a planar surface, the support assembly configured to impart motion to the carrier assembly in one or more of 1) yaw about a first axis that extends through the opening, 2) pitch about a second axis that is perpendicular to the first axis, 3) roll about a third axis that is perpendicular to the first and second axes, and 4) elevation changes above the support assembly;
the support assembly comprising:
a base platform;
a frame movably disposed on the base platform and operable to provide yaw about the first axis;
a joint having a lower yoke mounted on the frame and an upper yoke slideably coupled within the opening, the upper yoke configured to engage the opening to impart said rotation about the first axis to the carrier assembly based on rotation of the frame;
a plurality of motor assemblies mounted on the frame, each of the motor assemblies configured to engage the bottom surface of the support platform and being actuatable independently of each other; and
an electronic controller unit operable to control an operation of the plurality of motor assemblies to impart one or more of 1) pitch, 2) roll, and 3) elevation changes on the carrier assembly.

16. The rocker of claim 15, further comprising:
a rotation motor assembly mounted on one of the base platform and the frame, the rotation motor assembly operatively engaged with the other one of the base platform and the frame;
the electronic controller unit operable to control an operation of the rotation motor assembly to impart rotation on the frame and the carrier assembly.

17. The rocker of claim 15, wherein the electronic controller unit further comprises:
a transceiver for communicating with a wireless user interface for inputting a motion pattern;
the wireless user interface configured to send a signal corresponding to a motion pattern to the transceiver to impart the motion pattern on the support platform.

18. The rocker of claim 15, further comprising one or more sensors;
the one or more sensors configured to detect and to send a signal to the electronic controller unit;
the electronic controller unit configured to send a signal to a wireless user interface based on the signal from the sensor.

19. The rocker of claim 18, wherein the wireless user interface is configured to generate an alarm based on the signal from the electronic controller unit, the alarm including one or more of an audible alarm, a visual alarm and a tactile alarm.

20. The rocker of claim 19, wherein the wireless user interface is a wristband comprising a vibrating alarm.

* * * * *

UNITED STATES PATENT AND TRADEMARK OFFICE
CERTIFICATE OF CORRECTION

PATENT NO. : 10,702,073 B2
APPLICATION NO. : 15/901495
DATED : July 7, 2020
INVENTOR(S) : Steven Paperno Page 1 of 1

It is certified that error appears in the above-identified patent and that said Letters Patent is hereby corrected as shown below:

In the Claims

In Column 18 at Line 36, In Claim 6, change "3) a movement" to --2) a movement--.

In Column 18 at Line 40, In Claim 6, change "as least" to --at least--.

Signed and Sealed this
Fifteenth Day of September, 2020

Andrei Iancu
*Director of the United States Patent and Trademark Office*